United States Patent
Lee et al.

(10) Patent No.: US 11,642,366 B2
(45) Date of Patent: May 9, 2023

(54) METHODS FOR PREVENTING A SERIOUS HEALTH CONSEQUENCE AND/OR TISSUE DAMAGE AFTER EXPOSURE TO IONIZING RADIATION AND/OR CHEMOTHERAPY

(71) Applicant: GLYCOMIRA THERAPEUTICS, INC., Salt Lake City, UT (US)

(72) Inventors: Won Yong Lee, Bountiful, UT (US); Abigail Pulsipher, Salt Lake City, UT (US); Thomas P. Kennedy, Charlotte, NC (US); Justin Rodney Savage, North Salt Lake, UT (US); Glenn Prestwich, Spokane, WA (US)

(73) Assignee: GLYCOMIRA THERAPEUTICS, INC., Salt Lake City, UT (US)

( * ) Notice: Subject to any disclaimer, the term of this patent is extended or adjusted under 35 U.S.C. 154(b) by 97 days.

(21) Appl. No.: 17/059,982

(22) PCT Filed: Jun. 3, 2019

(86) PCT No.: PCT/US2019/035145
§ 371 (c)(1),
(2) Date: Nov. 30, 2020

(87) PCT Pub. No.: WO2019/236453
PCT Pub. Date: Dec. 12, 2019

(65) Prior Publication Data
US 2021/0228618 A1    Jul. 29, 2021

Related U.S. Application Data

(60) Provisional application No. 62/679,837, filed on Jun. 3, 2018.

(51) Int. Cl.
| | | |
|---|---|---|
| *A61K 31/727* | (2006.01) | |
| *A61P 39/00* | (2006.01) | |
| *A61K 31/728* | (2006.01) | |
| *A61K 31/737* | (2006.01) | |

(52) U.S. Cl.
CPC .......... *A61K 31/727* (2013.01); *A61K 31/728* (2013.01); *A61K 31/737* (2013.01); *A61P 39/00* (2018.01)

(58) Field of Classification Search
CPC ... A61K 31/727; A61K 31/728; A61K 31/737
See application file for complete search history.

(56) References Cited

U.S. PATENT DOCUMENTS

| | | | |
|---|---|---|---|
| 2003/0161884 A1 | 8/2003 | Rosenberg et al. | |
| 2004/0152662 A1* | 8/2004 | Pommerville | A61P 1/16 514/54 |
| 2007/0123480 A1 | 5/2007 | Kennedy et al. | |
| 2011/0000934 A1 | 1/2011 | Senner et al. | |
| 2012/0021968 A1 | 1/2012 | Oottamasathien et al. | |
| 2012/0077773 A1 | 3/2012 | Adolfsson et al. | |
| 2012/0201781 A1 | 8/2012 | Raiesh | |
| 2013/0035307 A1 | 2/2013 | Prestwich et al. | |
| 2013/0209531 A1* | 8/2013 | Prestwich | A61K 8/735 424/56 |
| 2015/0004131 A1 | 1/2015 | Milstein et al. | |
| 2016/0022060 A1 | 1/2016 | Canion | |
| 2016/0220601 A1 | 8/2016 | Klein | |
| 2016/0287626 A1* | 10/2016 | Marcus | A61P 7/06 |
| 2018/0075936 A1 | 3/2018 | Milstein et al. | |

FOREIGN PATENT DOCUMENTS

| | | |
|---|---|---|
| WO | 2011156445 A1 | 12/2011 |
| WO | 2015061358 A1 | 4/2015 |
| WO | 2018053111 A1 | 3/2018 |
| WO | 2018104950 | 6/2018 |
| WO | 2018104950 A1 | 6/2018 |

OTHER PUBLICATIONS

Gacci, M. et al "Bladder instillation therapy with hyaluronic acid and chondroitin sulfate . . . " Clin. Genitour. Cancer, vol. 14, No. 5, pp. 444-449. (Year: 2016).*
Pulsipher A, Savage JR, Kennedy TP, Gupta K, Cuiffo BG, Sonis ST, et al. (2021) GM-1111 reduces radiation-induced oral mucositis in mice by targeting pattern recognition receptormediated inflammatory signaling. PLoS One 16(3):e0249343.
Mangoni et al., "Differential Effect Triggered by a Heparan Mimetic of the RGTA Family Preventing Oral Mucositis Without Tumor Protection" Int. J. Radiation Oncology Biol. Phys. vol. 74. No. 4. pp. 1242-1250.2009. DOI:10.1016/j.ijrobp.2009.03.006.
Supplementary European Search Report Application No. EP 19816009 dated Jan. 14, 2022.
International Search Report and Written Opinion for PCT/US2019/35145 dated Aug. 19, 2019.

* cited by examiner

*Primary Examiner* — Leigh C Maier
(74) *Attorney, Agent, or Firm* — Thomas | Horstemeyer, LLP

(57) ABSTRACT

Described herein are methods for preventing a serious health consequence and/or tissue damage in a subject after the subject has been exposed to ionizing radiation and/or chemotherapy. The methods involve administering to the subject a sulfated polysaccharide or the pharmaceutically acceptable salt or ester thereof after the subject has been exposed to ionizing radiation and/or chemotherapy. The methods described herein are most beneficial to cancer patients who suffer from mucositis after exposure to ionizing radiation.

26 Claims, 12 Drawing Sheets

METHODS FOR PREVENTING A SERIOUS HEALTH CONSEQUENCE AND/OR TISSUE DAMAGE AFTER EXPOSURE TO IONIZING RADIATION AND/OR CHEMOTHERAPY

CROSS REFERENCE TO RELATED APPLICATIONS

This application claims priority upon U.S. provisional application Ser. No. 62/679,837, filed Jun. 3, 2018. This application is hereby incorporated by reference in its entirety.

ACKNOWLEDGMENTS

This invention was made with government support under Grant No. 2R44DE024024 awarded by the National Institute of Dental and Craniofacial Research. The government has certain rights in the invention.

BACKGROUND

Mucositis is an inflammatory disease of a mucosal tissue. It develops when a subject is exposed to ionizing radiation and/or chemotherapy. Cancer patients undergoing radiation therapy and chemotherapy can suffer from a number of different types of mucositis as well. For example, mucositis can form in the mouth and gastrointestinal tract during radiation and chemotherapy. Oral mucositis progresses from erythema within a week after cancer therapy and quickly turns into ulcerative lesions with opportunistic infections causing severe pain and difficulty in eating. These severe clinical outcomes lead to therapy interruptions, therapeutic dose reductions, and emergency room visits and most patients resort to narcotic medications for pain relief. Mucositis occurs in over 80% of patients receiving radiation therapy for head and neck cancer. Severe mucositis limits food intake, leading to a 2-fold increase in weight loss and a 4-fold increase in the rate of tube feeding. Unplanned emergency visits, increased opioid use, and hospitalization significantly increase the cost of treatment.

Exposure to ionizing radiation can also cause other serious health consequences leading to acute radiation syndrome (ARS). Affected people typically develop life threatening conditions such as hematopoietic (HP), gastrointestinal (GI), and cardiovascular/central nervous system (CV/CNS) syndromes depending on the exposed level of ionizing radiation. The rapid progression of the disease as well as the potential long-term effects on the health of the survivors presents a tremendous challenge. In addition, the cost of medical care for ARS can be extremely prohibitive to patients. The financial burden can be a serious problem to society.

The source of the ionizing radiation can vary. While radiation treatment of cancer patients is predictable, there are other situations where the population may be exposed to ionizing radiation. For example, an accidental breach at a nuclear facility may expose workers to high levels of ionizing radiation. Nuclear threats from hostile countries also increase the likelihood that the population can be exposed to ionizing radiation.

It is imperative to develop effective medical countermeasures for ionizing radiation exposure in the medical field as well as protecting the public from unexpected exposure to ionizing radiation.

SUMMARY

Described herein are methods for preventing a serious health consequence and/or tissue damage in a subject after the subject has been exposed to ionizing radiation and/or chemotherapy. The methods involve administering to the subject a sulfated polysaccharide or the pharmaceutically acceptable salt or ester thereof after the subject has been exposed to ionizing radiation and/or chemotherapy. The methods described herein are most beneficial to cancer patients who suffer from mucositis after exposure to ionizing radiation.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
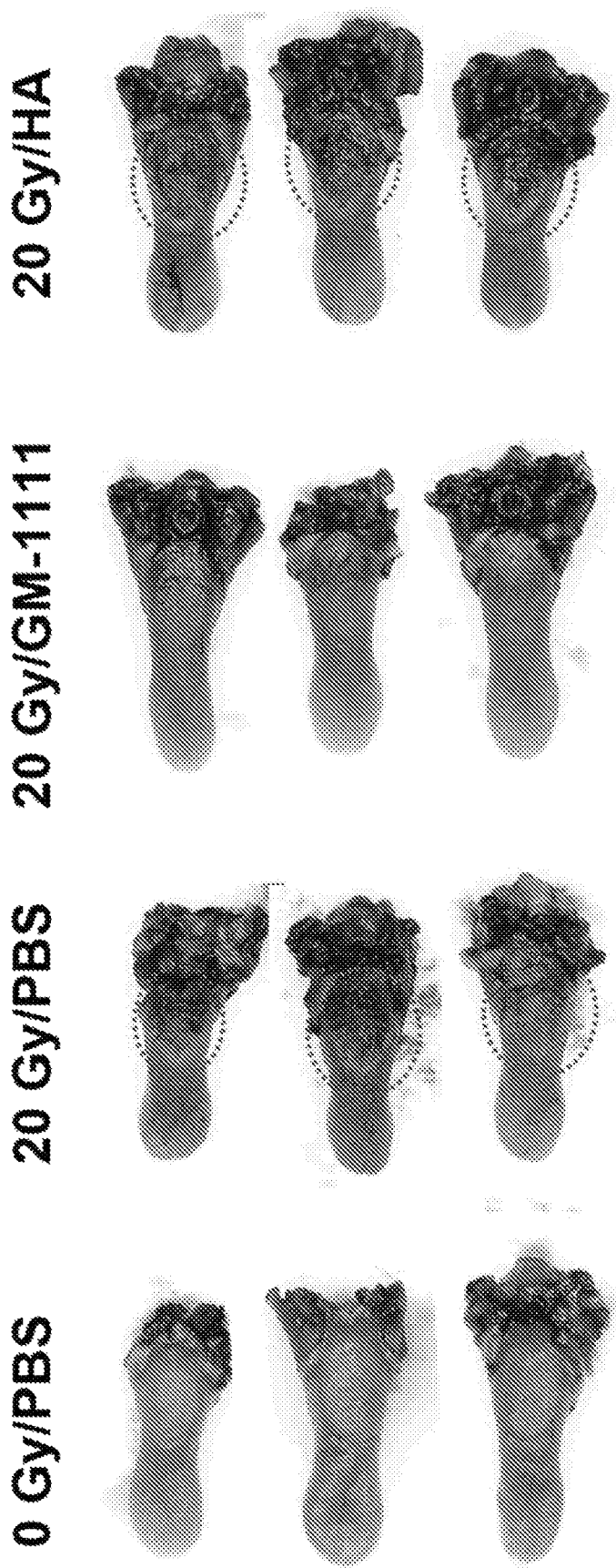
FIG. 1 shows a mouse (BDF1 male) tongues (8 days after the x-ray irradiation) stained with Toluidine Blue to visualize the ulcerated lesions (marked by dotted red ovals). The tongues from vehicle (PBS) treated animals show severely ulcerated lesions. GM-1111 treated (30 mg/kg, body weight, once daily SQ from 2 days prior to the irradiation (day 0) to day 7) animals had smaller lesions in the tongue than the vehicle or HA treated animals. The cut surfaces created during the dissection (excision wound) also show strong Toluidine Blue staining (back edges).

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

As used herein, the term "about" is used to provide flexibility to a numerical range endpoint by providing that a given value may be "a little above" or "a little below" the endpoint without affecting the desired result.

Throughout this specification, unless the context dictates otherwise, the word "comprise," or variations such as "comprises" or "comprising," will be understood to imply the inclusion of a stated element, integer or step, or group of elements, integers or steps but not the exclusion of any other element, integer or step, or group of elements, integers or steps.

A "subject" as used in the specification and concluding claims, refers to a human or non-human animal. For example, the subject is a non-human animal (domesticated, wild, farm) such as, for example, a horse, cat, dog, cow, pig, sheep, goat, mouse, rabbit, chicken, rat, or guinea pig.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, hyaluronan that contains at least one —OH group can be represented by the formula Y-OH, where Y is the remainder (i.e., residue) of the hyaluronan molecule.

The term "ionizing radiation" as used herein is defined radiation that has sufficient energy to eject one or more orbital electrons from an atom or molecule (e.g., alpha particles, beta particles, gamma rays, x-rays, neutrons, protons, and other particles having sufficient energy to produce ion pairs in matter. Absorbed doses are typically measured in "grays" (Gy).

In one aspect, the source of ionizing radiation can be produced during the production of nuclear energy. In one aspect, ionizing radiation is produced during the mining and milling of uranium. Solid and liquid waste produced during the milling and mining process also can produce ionizing radiation. In another aspect, uranium enrichment and fuel fabrication processes can produce ionizing radiation. In another aspect, nuclear reactors and an accidental breach thereof is a source of ionizing radiation. In another aspect, the reprocessing of spent fuel to separate out and recover usable uranium and plutonium from the waste is another source of ionizing radiation. In another aspect, solid waste produced during the various stages of in the nuclear fuel cycle can produce ionizing radiation. In another aspect, the source of the ionizing radiation can be derived from maintaining or servicing nuclear power plant. In one aspect, the ionizing radiation can be exposure to radioactivity resulting from an atomic detonation test, a terrorist act, or an act of war.

In one aspect, the source of ionizing radiation can involve the transport and storage of radioactive materials. Radioactive materials of natural and artificial origin are used widely around the world and are transported within and between countries. Radioactive materials include but are not limited to radiopharmaceuticals for medical applications to radioactive spent fuel. Transport of the radioactive materials can be by land, sea, or air.

In one aspect, the source of ionizing radiation is from the production and use of radioisotopes in industry, medicine, and research. Radiation is used for both for diagnostic and therapeutic purposes. Here the patient and the health-care provider are exposed to radiation. In one aspect, diagnostic radiology such as the use of X-rays and organ imaging using radionuclide generators such as $^{99m}$Tc generators can be a source of ionizing energy. In other aspects, therapeutic uses of radionuclides (i.e., radiotherapy) can be a source of ionizing energy. Cancer patients undergoing radiotherapy as well health-care providers are exposed to elevated doses of radiation. In one aspect, the cancer patient is exposed to radiation via a linear accelerator, betatron, or microtron, which is referred to as teletherapy. In another aspect, the cancer patient undergoes brachytherapy, where radioactive sources are placed within the body of the patient so that the radiation source is close to the tissue to be treated.

In one aspect, the ionizing radiation is cosmic radiation. For example, astronauts that are involved in extraterrestrial travel or residence are exposed to cosmic radiation. In one aspect, the cosmic radiation is galactic cosmic radiation, which arises from outside the solar system from deep space. Galactic cosmic radiation can have an energy spectrum of $10^8$ eV to more than $10^{15}$ eV. In another aspect, the cosmic radiation is solar cosmic radiation, which is generated near the surface of the sun by magnetic disturbances In one aspect, a subject can be exposed to ionizing radiation in the form radioisotopes when extracting and/or processing certain ores. In one aspect, the mining of metals such as aluminum, copper, iron, steel, lead, niobium, tin, zinc, and gold can produce radioisotopes such as, for example, $^{232}$Th and $^{228}$Ra. The concentration of radioisotopes in intermediary products and wastes will depend upon the initial content of the radioisotopes present in the ore and the process used to extract the metal. In one aspect, the mining of phosphate as a source of phosphorous for fertilizer can produce radioisotopes such as, for example, $^{232}$Th, $^{238}$U, $^{210}$Pb, $^{210}$Po, and $^{228}$Ra. In one aspect, the mining of coal and the burning of coal can produce radioisotopes such as, for example, $^{232}$Th and $^{228}$Ra. In one aspect, the extraction of rare earth metals can produce radioisotopes such as, for example, $^{232}$Th and $^{238}$U. In one aspect, the extraction of oil and natural gas can produce radioisotopes such as, for example, $^{232}$Th, $^{222}$Rh, $^{210}$Pb, $^{210}$Po, $^{226}$R, and $^{228}$Ra. In one aspect, the mining of zircon and zirconia can produce radioisotopes such as, for example, $^{232}$Th and $^{228}$Ra. In one aspect, the mining of radium and thorium can produce radioisotopes such as, for example, $^{232}$Th and $^{228}$Ra.

The term "chemotherapy" as used herein is defined as a category of cancer treatment that involves the administration of one or more anti-cancer drugs (chemotherapeutic agents) as part of a standardized chemotherapy regimen.

The term "prevent" as used herein is defined as eliminating or reducing the likelihood of the occurrence of one or more symptoms associated with exposure to ionizing radiation and/or chemotherapy (e.g., a serious health consequence, tissue damage) when compared to the same subject that has not been administered a sulfated polysaccharide as described herein. The term "prevent" also includes the reduction in the severity of one or more symptoms associated with exposure to ionizing radiation and/or chemotherapy when compared to the same subject that has not been administered a sulfated polysaccharide as described herein.

A weight percent of a component, unless specifically stated to the contrary, is based on the total weight of the formulation or composition in which the component is included.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an illustration, a numerical range of "about 1 to about 5" should be interpreted to include not only the explicitly recited values of about 1 to about 5, but also to include individual values and sub-ranges within the individual range. Thus, included in this numerical range are individual values such as 2, 3, and 4, the sub ranges such as from 1-3, from 2-4, from 3-5, etc., as well as 1, 2, 3, 4, and 5 individually. The same principle applies to ranges reciting only one numerical value as a minimum or maximum. Furthermore, such an interpretation should apply regardless of the breadth of the range or the characteristics being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each various individual and collective combination and permutation of these compounds may not be explicitly disclosed, each is specifically contemplated and described herein. For example, if a class of silk-elastinlike proteins A, B, and C are disclosed, as well as a class of semi-synthetic glycosaminoglycans (GAGs) D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

Described herein are methods for preventing a serious health consequence, and/or tissue damage in a subject after the subject has been exposed to ionizing radiation and/or chemotherapy. The methods involve administering to the subject a sulfated polysaccharide or the pharmaceutically acceptable salt or ester thereof after the subject has been exposed to ionizing radiation and/or chemotherapy. In one aspect, the methods described herein are beneficial to cancer patients who suffer from mucositis after exposure to ionizing radiation and/or chemotherapy. In another aspect, the methods described herein can also be used as a countermeasure in situations where a subject has been accidentally or intentionally exposed to ionizing radiation.

Not wishing to be bound by theory, the earliest injury to the subject after exposure to ionizing radiation or chemotherapy is to the endothelium, followed by infiltration of inflammatory cells into submucosal tissues. One possible model of mucositis suggests disease progression through five phases: (i) an initiation phase with release of damage-associated pattern (DAMP) molecules that initiate toxicity through the innate immune system and formation of reactive oxygen species that activate transcription factors and genes associated with inflammatory cytokines, (ii) a primary damage response phase during which further pro-inflammatory mediators are activated, resulting in apoptosis of cells of the basal epithelium, (iii) an amplification phase mediators generated in previous phases, (iv) an ulceration phase with epithelial breakdown from apoptosis, robust infiltration of inflammatory leukocytes, and bacterial infection, and (v) a healing phase that is characterized by cell proliferation.

It has been unexpectedly discovered that the administration of a sulfated polysaccharide or the pharmaceutically acceptable salt or ester thereof described herein to a subject after exposure to ionizing radiation and/or chemotherapy prevents or significantly prevents or reduces a serious health consequence and/or tissue damage.

In one aspect, the methods described herein can prevent a serious health consequence in a subject that has been exposed to ionizing energy. A "serious health consequence" is one or more adverse conditions caused by exposing the subject to ionizing energy. The conditions can be related to one another (e.g., the first condition causes a subsequent second condition) or they can be independent of one another. In one aspect, the serious health consequence is acute radiation syndrome (ARS). Subjects with ARS can have hematopoietic syndrome, gastrointestinal syndrome, rhinosinal syndrome, and/or cardiovascular/central nervous system syndromes. In other aspects, the serious health consequence involves damage to the renal system, hepatic system, musculoskeletal system, endocrine system, reproductive system, and sensory system (e.g., taste, smell, etc.).

Not wishing to be bound by theory, the onset of GI syndrome is thought to start with the gut epithelial tissue damage. Irradiation causes radiosensitive cell populations to undergo cell death. The resulting loss of functional villi leads to diarrhea and malabsorption of nutrients. The destroyed mucosal barrier allows bacterial invasion into the tissues eventually leading to septicemia. Irradiation can induce endothelial cells to release potent pro-inflammatory cytokines that initiate various local (gut) as well as systemic changes. The eventual loss of function in many organs due to sepsis eventually leads to life threatening multiple organ dysfunction syndrome (MODS).

In one aspect, the methods described herein can prevent tissue damage in a subject that has been exposed to ionizing energy. In one aspect, the methods described herein can prevent damage to the epithelium in the subject. In another aspect, the methods described herein can prevent damage to a mucosal membrane in the subject. In another aspect, the methods described herein can prevent damage to tissue in the mouth, salivary glands, mucosal glandular tissues, sinus, lungs, intestine, vagina, anus, rectum, or urinary tract of the subject. In another aspect, the methods described herein can prevent proctitis or sinusitis induced by ionizing radiation and/or chemotherapy. In another aspect, the methods described herein can prevent damage to skin of the subject.

In one aspect, the methods described herein are effective in preventing mucositis and reducing the symptoms of mucositis after exposure to ionizing radiation and/or chemotherapy. For example, the methods described herein are effective in preventing oral mucositis. Patients with neck and head cancer exposed to ionizing radiation and/or chemotherapy are susceptible to oral mucositis, which has several symptoms including, but not limited to, formation of ulcers in the mouth and tongue, epithelial death of the oral mucosa, reduced thickness of the oral mucosa, swollen gums, or infection of the oral mucosa. The methods described herein can prevent these symptoms and provide relief to the subject.

Another feature of the methods described herein is that the sulfated polysaccharide or the pharmaceutically acceptable salt or ester thereof does not need to be administered immediately after exposure to ionizing radiation and/or chemotherapy. This is an important feature in situations where the subject has been accidentally exposed to ionizing radiation or exposed to ionizing radiation due to a terrorist attack or act of war.

In one aspect, the sulfated polysaccharide is initially administered to the subject within 0.5 hours to 72 hours after the initial exposure to ionizing radiation and/or chemotherapy. In another aspect, the sulfated polysaccharide is initially administered to the subject 0.5 hours, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 30 hours, 36 hours, 42 hours, 48 hours, 60 hours, or 72 hours where any value can be a lower and upper-endpoint of a range (e.g., 12 hours to 24 hours).

The sulfated polysaccharide or the pharmaceutically acceptable salt or ester thereof can be administered once a day or multiple times per day (e.g., 2×, 4×, 8× daily or every other day). The sulfated polysaccharide can be administered over a period of time depending upon the amount of exposure to ionizing radiation and/or chemotherapy. In one aspect, the sulfated polysaccharide or the pharmaceutically acceptable salt or ester thereof is administered to the subject daily for up to 28 days after exposure to the ionizing radiation and/or chemotherapy. In another aspect, the sulfated polysaccharide or a pharmaceutically acceptable salt or ester thereof is administered to the subject daily or every other day for 2 days, 3 days, 4 days, 5 days, 6 days, 7 days, 8 days, 9 days, 10 days, 12 days, 14 days, 16 days, 18 days, 20 days, 22, days, 24 days, 26 days, or 28 days after exposure to the ionizing radiation and/or chemotherapy, where any value can be a lower and upper-endpoint of a range (e.g., 2 days to 8 days).

In certain aspects, the sulfated polysaccharide or a pharmaceutically acceptable salt or ester thereof is administered prior to exposure to the ionizing radiation as well as after exposure to the ionizing radiation. In one aspect, the sulfated polysaccharide or a pharmaceutically acceptable salt or ester thereof is administered to the subject up to three days prior to exposure to the ionizing radiation.

The sulfated polysaccharide useful herein is a polymeric carbohydrate molecule composed of long chains of monosaccharide units bound together by glycosidic linkages, where one or more sulfate groups are covalently bonded to the polysaccharide. The sulfated polysaccharide can be a naturally-occurring molecule or a synthetic analogue. In the case when the sulfated polysaccharide is a synthetic analogue, additional chemical modifications to the sulfated polysaccharide can be performed (e.g., chemical modification of carboxyl and hydroxyl groups, oxidative ring opening, etc.). Sulfation of a naturally-occurring or synthetic polysaccharide can be performed using techniques known in the art. When the sulfated polysaccharide has been chemically-modified, sulfation of the chemically-modified polysaccharide can occur before and/or after chemical modification.

In one aspect, the sulfated polysaccharide or a pharmaceutically acceptable salt or ester thereof is a sulfated glycosaminoglycan. Generically, GAGs are represented by the formula A-B-A-B-A-B, where A is an uronic acid and B is an aminosugar that is either O- or N-sulfated, where the A and B units can be heterogeneous with respect to epimeric content or sulfation. In one aspect, the sulfated glycosaminoglycan is chondroitin sulfate, dermatan sulfate, heparin, dermatan sulfate, and heparan sulfate, or any combination thereof.

In another aspect, the glycosaminoglycan is non-sulfated that can be subsequently sulfated. Hyaluronan is an example of a non-sulfated glycosaminoglycan that can be sulfated. Chondroitin produced by invertebrates is another example of a non-sulfated glycosaminoglycan that can be sulfated.

In one aspect, the sulfated polysaccharide or a pharmaceutically acceptable salt or ester thereof is a heparinoid. Heparinoids are glycosaminoglycans that are derivatives of heparin. They include oligosaccharides and sulfated polysaccharides of plant, animal, or synthetic origin.

In one aspect, the sulfated polysaccharide is a synthetic heparinoid or other synthetic or semisynthetic GAG-like compound such as, for example, Pixatimod (PG545, a glucopyranose tetrasaccharide from Zucero Therapeutics), Muparfostat (PI-88, a phosphomannopentaose and phosmannotetraose sulfate mixture from Medigen Biotechnology), Roneparstat (SST0001, a glycol split heparin from Leadiant Biosciences), Necuparanib (M402, a glycol split heparin from Momenta Pharmaceuticals), CS-01 (a 2,3-O-desulfated heparinfrom Cantex Pharmaceuticals), Tafoxiparin (DF01, a low molecular weight glycol-split heparin from Dilafor), Sevuparin (a glycol-split heparin from Modus Therapeutics), SB-030 and SB-061 (respectively, a peptide-modified heparin and a peptide-modified chondroitin sulfate from Symic Bio), OTR4120 (a modified dextran containing sulfate and carboxylate groups from OTR3), ELMIRON® (pentosan polysulfate, a chemically sulfated xylan from Janssen Phramaceuticals), Danaparoid sodium (ORGARAN® from Aspen Pharma), Dalteparin (FRAGMIN® from Pharmacia AB), Nadroparin, Enoxaparin (LOVENOX® from Aventis Pharma SA), Tinzaparin, Sulodexide, Fondaparinux (ARIXTRA® from Mylan Institutional), and mixtures thereof. Structures of some of these synthetic heparinoids and related molecules are presented in Table 1.

TABLE 1
Structures of Some Synthetic Heparinoids
| Name | Developer | Structure |
| --- | --- | --- |
| PIXATIMOD | Zucero Therapeutics | 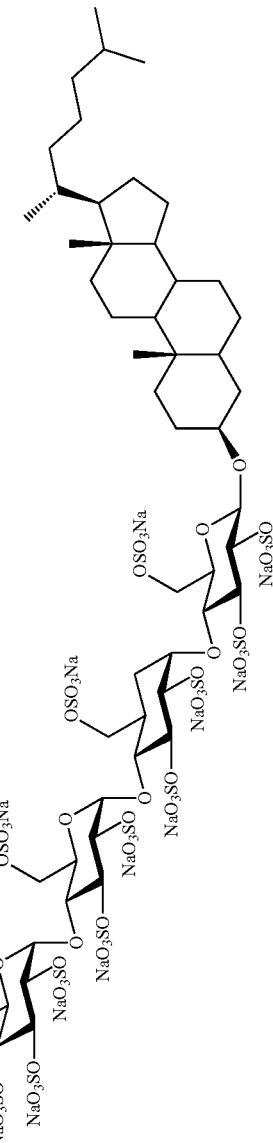 |
| MUPARFOSTAT | Medigen Biotechnology | 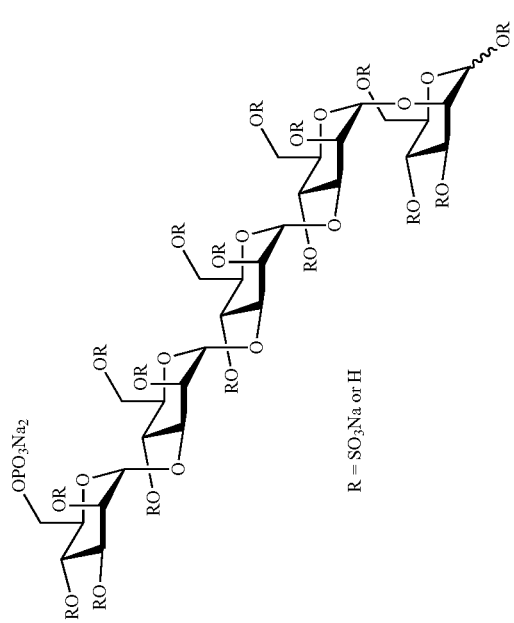 |

TABLE 1-continued

Structures of Some Synthetic Heparinoids

| Name | Developer | Structure |
|---|---|---|
| RONEPARSTAT | Leadiant Biosciences | (chemical structure) $n + p + m = 25-30$; R = 30%, H = 70%, SO$_3$; R$_2$ around 91% H, 9% SO$_3$ |
| NECUPARANIB | Momenta Pharmaceuticals | (chemical structure) $n + p + m$ around 10; R = 30% H, 70% SO$_3^-$; R$_2$ = 80% SO$_3$; 20% Ac, R$_2$ around 91%H, 9%SO$_3^-$ |

TABLE 1-continued

Structures of Some Synthetic Heparinoids

| Name | Developer | Structure |
|---|---|---|
| CS-01 | Cantex | 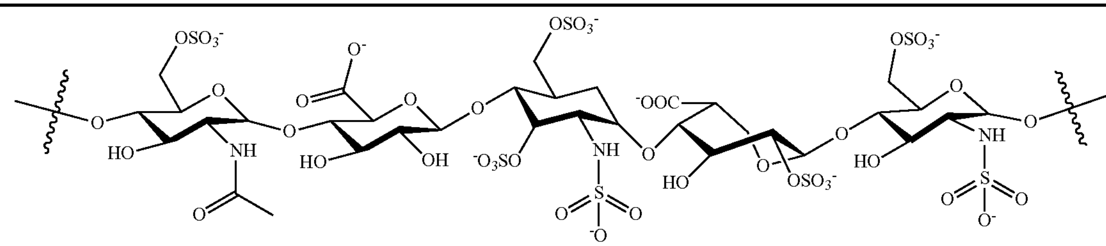 |
| TAFOXIPARIN | Dilafor | 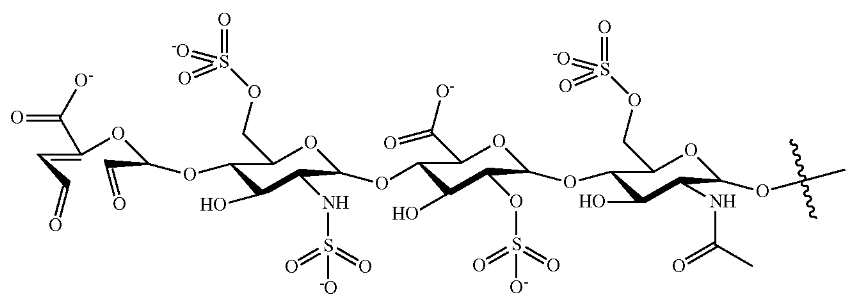 |
| SEVUPARIN | Modus Therapeutics | 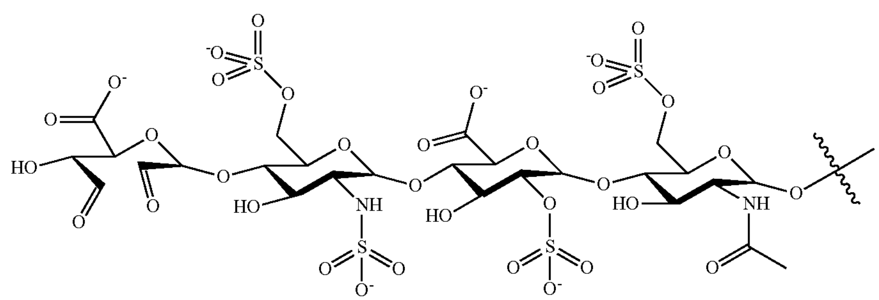 |

TABLE 1-continued
Structures of Some Synthetic Heparinoids
| Name | Developer | Structure |
|------|-----------|-----------|
| SB-030 | Symic Bio | 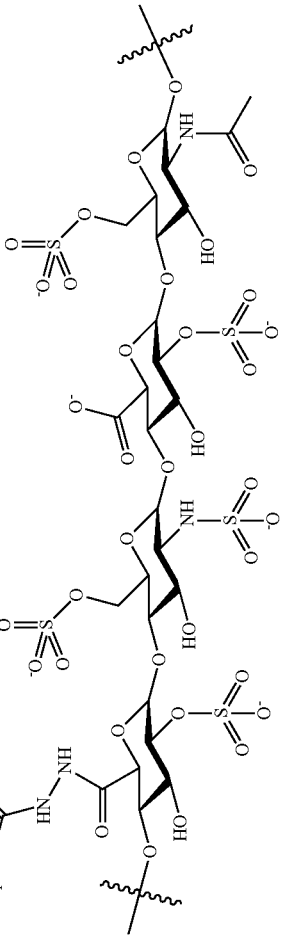 |
| SB-061 | Symic Bio | 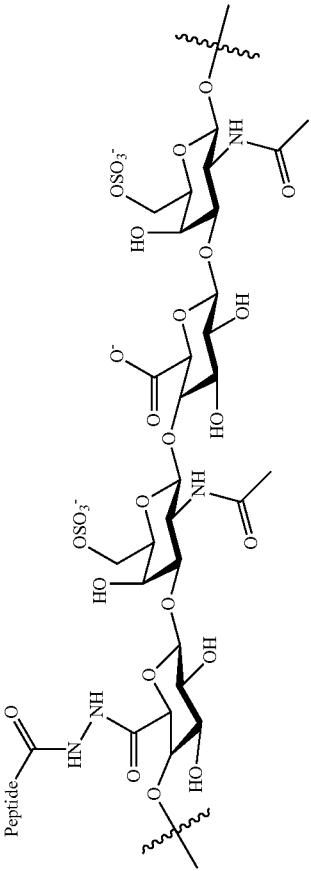 |

TABLE 1-continued
Structures of Some Synthetic Heparinoids
| Name | Developer | Structure |
|---|---|---|
| OTR4120 | OTR3 | 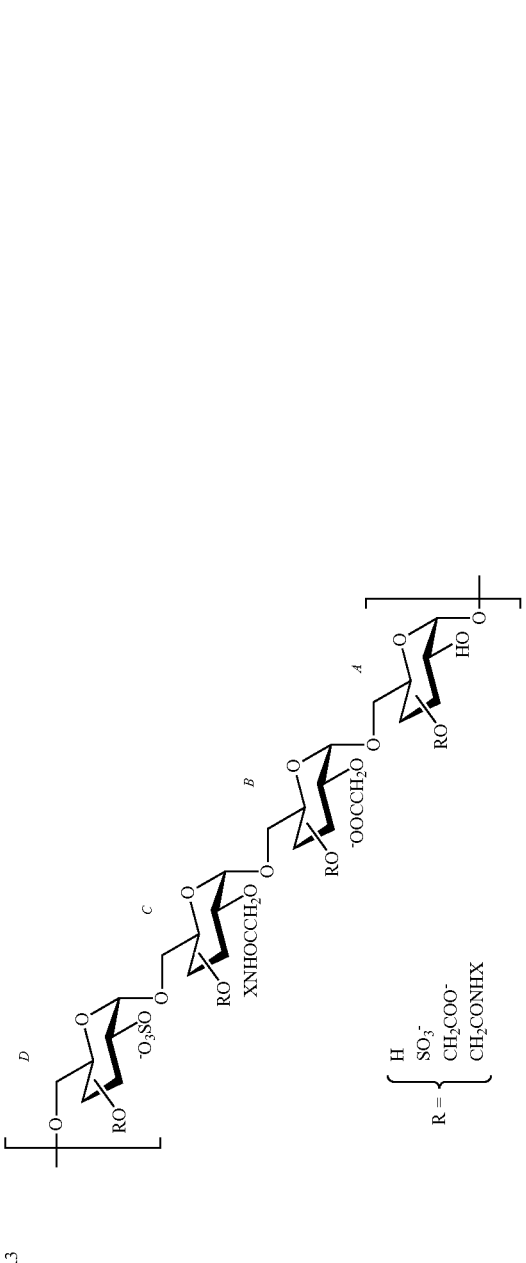 OTR4120 composition: A < 1%, B = 33%, C = 0% and D = 87% |
| ELMIRON ® | Janssen Pharmaceuticals | 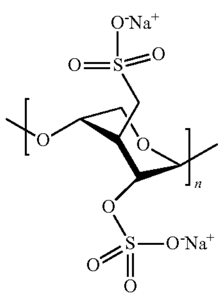 |

In one aspect, the sulfated polysaccharide or a pharmaceutically acceptable salt or ester thereof is a heparan sulfate analogue, which is also referred to as ReGeneraTing Agents (RGTA). RGTAs are synthetic biomimetics of glycosaminoglycans. In one aspect, the RGTA is OTR4120 ($\alpha(1\rightarrow 6)$ polycarboxylmethylsulfate glucose), which is a water-soluble dextran derivative that contains carboxymethyl and sulfate groups with degrees of substitution (DS) of 0.50 and 1.30, respectively. In another aspect, the RGTA is OTR4131 ($\alpha(1\rightarrow 6)$ polycarboxylmethylsulfateacetate glucose)

In one aspect, the sulfated polysaccharide is a sulfated hyaluronan or the pharmaceutically acceptable salt or ester thereof. In one aspect, the sulfated hyaluronan has a degree of sulfation from 0.1 to 4.0 per disaccharide unit. In another aspect, the sulfated hyaluronan has a degree of sulfation from 0.1, 0.5, 1.0, 1.5, 2.0, 2.5, 3.0, 3.1, 3.2, 3.3, 3.4, 3.5, 3.6, 3.7, 3.8, 3.9, or 4.0 per disaccharide unit, where any value can be a lower and upper end-point of a range (e.g., 3.0 to 4.0, 3.2 to 3.8, etc.).

In another aspect, the average molecular weight of the sulfated hyaluronan is less than 1,000 kDa, less than 900 kDa, less than 800 kDa, less than 700 kDa, less than 600 kDa, less than 500 kDa, less than 400 kDa, less than 300 kDa, less than 200 kDa, less than 100 kDa, less than 50 kDa, less than 25 kDa, less than 10 kDa, or less than 5 kDa. In another aspect, the sulfated hyaluronan has an average molecular size from 0.5 kDa to less than 50 kDa, 2 Da to 20 kDa, or 3 kDa to 10 kDa. In a further aspect, the sulfated hyaluronan has an average molecular size from 0.5 kDa to 10 kDa or 1 kDa to 5 kDa. Depending upon reaction conditions, one or more different hydroxyl groups present in the low molecular hyaluronan or hyaluronan oligosaccharide can be sulfated. In one aspect, the primary C-6 hydroxyl proton of the N-acetyl-glucosamine residue of the low molecular hyaluronan or hyaluronan oligosaccharide is sulfated. In another aspect, the primary C-6 hydroxyl proton of the N-acetyl-glucosamine residue of hyaluronan and at least one C-2 hydroxyl proton or C-3 hydroxyl proton of a uronic acid residue or at least one C-4 hydroxyl proton of an N-acetyl-glucosamine residue is substituted with a sulfate group. In another aspect, the primary C-6 hydroxyl proton of the N-acetyl-glucosamine residue of the low molecular hyaluronan or hyaluronan oligosaccharide and at least one C-2 hydroxyl proton and C-3 hydroxyl proton of a uronic acid residue and at least one C-4 hydroxyl proton of an N-acetyl-glucosamine residue is substituted with a sulfate group. In another aspect, 0.001%, 0.01%, 0.1%, 1%, 5%, 10%, 20%, 30%, 40%, 50%, 60%, 70%, 80%, 90%, 95%, or less than 100%, or any range thereof of hydroxyl protons present on the low molecular hyaluronan or hyaluronan oligosaccharide can be deprotonated and subsequently sulfated.

In another aspect, the sulfated hyaluronan has (1) 100% of the primary C-6 hydroxyl protons of the N-acetyl-glucosamine residue of the sulfated hyaluronan are substituted with a sulfate group, (2) a degree of sulfation from 3.0 to 4.0, and (3) an average molecular weight from 1 kDa to 3 kDa.

The hyaluronan starting material used to produce the sulfated hyaluronan can exist as the free acid or the salt thereof. Derivatives of hyaluronan starting material can also be used herein. The derivatives include any modification of the hyaluronan prior to sulfation. A wide variety of molecular weight hyaluronans can be used herein for the depolymerization step. In one aspect, the hyaluronan has a molecular weight greater than 1,000 kDa prior to depolymerization. In another aspect, the hyaluronan can have a molecular weight of 10 kDa to 1,000 kDa prior to depolymerization. A wide variety of hyaluronan molecular weights can also be employed for the sulfation step. In one aspect, the hyaluronan starting material can be converted to low molecular hyaluronan or a hyaluronan oligosaccharide prior to sulfation to produce the partially or fully sulfated hyaluronan. As will be discussed in greater detail below, low molecular weight hyaluronan is hyaluronan that has been degraded with an acid or base. Alternatively, hyaluronan oligosaccharide is produced by degrading hyaluronan with an enzyme such as, for example, hyaluronan synthase or hyaluronidase in a controlled fashion. Subsequently, hyaluronan oligosaccharides having different molecular weights can be separated by GPC or ion exchange separation. Exemplary procedures for producing low molecular weight hyaluronan or hyaluronan oligosaccharide from hyaluronan are provided in WO 2011/156445.

In one aspect, the low molecular hyaluronan or hyaluronan oligosaccharide being sulfated has a molecular weight from 1 kDa to 2,000 kDa. In another aspect, the low molecular hyaluronan or hyaluronan oligosaccharide being sulfated has a molecular weight from 5 kDa to 500 kDa, 10 kDa to 200 kDa, or 20 kDa to 100 kDa. Exemplary procedures for preparing low molecular weight hyaluronan are provided in WO 2011/156445. As discussed above, the molecular weight of the hyaluronan can be modified by cleaving hyaluronan with an acid or base to produce lower molecular weight hyaluronan. In certain aspects, the hyaluronan starting material or a derivative thereof is not derived from an animal source. In these aspects, the hyaluronan can be derived from other sources such as bacteria. For example, a recombinant *B. subtilis* expression system can be used to produce the hyaluronan starting material.

After the low molecular hyaluronan or hyaluronan oligosaccharide has been treated with a base, it is reacted with a sulfating agent to produce the partially or fully sulfated hyaluronan. Sulfating agents commonly used in organic synthesis can be used herein. Examples of sulfating agents include, but are not limited to, pyridine-sulfur trioxide complex or the triethylamine-sulfur trioxide complex. In one aspect, low molecular hyaluronan or hyaluronan oligosaccharide can be converted to the tributylamine salt, lyophilized, resuspended in dimethylformamide, and subsequently treated with a sulfating agent (e.g., pyridine-sulfur trioxide complex) to sulfate one or more hydroxyl protons.

In one aspect, when the sulfating agent is a pyridine-sulfur trioxide complex, a pyridinium adduct of the sulfated hyaluronan is produced, where pyridine is covalently attached to the sulfated hyaluronan. Not wishing to be bound by theory, when hyaluronan is reacted with the pyridine-sulfur trioxide complex in a solvent such as, for example, DMF, a small amount of acid is produced from traces of water present in situ, which causes partial depolymerization resulting in a free reducing end group. The hydroxyl group of the hemiketal can ultimately be sulfated to produce a sulfated intermediate, which subsequently reacts with free pyridine produced in situ to produce the pyridinium adduct. Thus, the sulfated hyaluronan used herein can include a mixture of sulfated hyaluronan that does not have pyridine covalently attached to the molecule and sulfated hyaluronan that does have pyridine covalently attached to the molecule. In one aspect, from 0.01% to 100%, 0.1% to 10%, or 0.15% to 2.5% of the sulfated hyaluronan has pyridine covalently attached to the molecule. In another aspect, the molecular weight of the pyridinium adduct of the sulfated hyaluronan is less than or equal to 10 kDa. In other aspects, the molecular weight is 0.1 kDa, 0.5 kDa, 1 kDa, 2 kDa, 3 kDa, 4 kDa, 5 kDa, 6 kDa, 7 kDa, 8 kDa, 9 kDa, or 10 kDa, where any value can for the lower and upper end-point of a molecular weight range.

In another aspect, the sulfated polysaccharide is hyaluronan or its pharmaceutically acceptable salt or ester having at least one sulfate group and at least one primary C-6 hydroxyl position of an N-acetyl-glucosamine residue comprising an alkyl group or fluoroalkyl group.

In one aspect, at least one primary C-6 hydroxyl proton of the N-acetyl-glucosamine residue of hyaluronan is substituted with an alkyl group. The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. In one aspect, the alkyl group is a $C_1$-$C_{10}$ branched or straight chain alkyl group. In a further aspect, the alkyl group is methyl. The alkyl group can be unsubstituted or substituted. In the case when the alkyl group is substituted, one or more hydrogen atoms present on the alkyl group can be replaced with or more groups including, but not limited to, alkynyl, alkenyl, aryl, halide, nitro, amino, ester, ketone, aldehyde, hydroxy, carboxylic acid, aralkyl, or alkoxy.

In another aspect, at least one primary C-6 hydroxyl proton of the N-acetyl-glucosamine residue of hyaluronan is substituted with a fluoroalkyl group. The term "fluoroalkyl group" as used herein is a branched or unbranched saturated hydrocarbon group of 1 to 24 carbon atoms, wherein at least one of the hydrogen atoms is substituted with fluorine. In certain aspects, the fluoroalkyl group includes at least one trifluoromethyl group. In other aspects, the fluoroalkyl group has the formula —$CH_2(CF_2)_nCF_3$, wherein n is an integer of 1, 2, 3, 4, 5, 6, 7, 8, 9, or 10. In one aspect, the fluoroalkyl group is —$CH_2CF_2CF_3$ or —$CH_2CF_2CF_2CF_3$.

In one aspect, the methylated/sulfated hyaluronan has the formula depicted below:

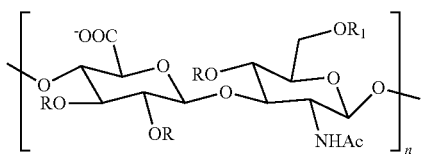

where $R_1$ is a methyl group, while the remaining R groups are sulfate groups alone or in combination with hydrogen. In one aspect, the n is from 5 to 20, 5 to 15, 5 to 10, or 7 to 9.

Alkylated and fluoroalkylated hyaluronan useful herein as well as methods for making the same are provided in WO2009/124266. The hyaluronan starting material can exist as the free acid or the salt thereof. Derivatives of hyaluronan starting material can also be used herein. The derivatives include any modification of the hyaluronan prior to the alkylation or fluoroalkylation step. A wide variety of molecular weight hyaluronan can be used herein. In one aspect, the hyaluronan has a molecular weight greater than 10 kDa prior to alkylation or fluoroalkylation. In another aspect, the hyaluronan has a molecular weight from 25 kDa to 1,000 kDa, 100 kDa to 1,000 kDa, 25 kDa to 500 kDa, 25 kDa to 250 kDa, or 25 kDa to 100 kDa prior to alkylation or fluoroalkylation. In certain aspects, the hyaluronan starting material or a derivative thereof is not derived from an animal source. In these aspects, the hyaluronan can be derived from other sources such as bacteria. For example, a recombinant B. subtilis expression system can be used to produce the hyaluronan starting material.

The hyaluronan starting material or derivative thereof is initially reacted with a sufficient amount of base to deprotonate at least one primary C-6 hydroxyl proton of the N-acetyl-glucosamine residue. The selection of the base can vary. For example, an alkali hydroxide such as sodium hydroxide or potassium hydroxide can be used herein. The concentration or amount of base can vary depending upon the desired degree of alkylation or fluoroalkylation. In one aspect, the amount of base is sufficient to deprotonate at least 0.001% of the primary C-6 hydroxyl protons of the N-acetyl-glucosamine residue of the hyaluronan starting material or derivative thereof. In other aspects, the amount of base is sufficient to deprotonate from 0.001% to 50%, 1% to 50% 5% to 45%, 5% to 40%, 5% to 30%, 5% to 20%, 10% to 50%, 20% to 50%, or 30% to 50% of the primary C-6 hydroxyl protons of the N-acetyl-glucosamine residue of the hyaluronan starting material or derivative thereof. It is understood that the more basic the solution, the more likely are chain cleavage reactions and the higher the degree of alkylation/fluoroalkylation that can be achieved. For example, other hydroxyl groups present on hyaluronan (e.g., 2-OH and/or 3-OH can be alkylated or fluoroalkylated). In one aspect, all of the hydroxyl groups present on hyaluronan can be alkylated or fluoroalkylated. In other aspects, 0.001%, 0.01%, 0.1%, 1%, 5%, 10%, 20%, 30%, 40%, 50%, 60%, 70%, 80%, 90%, 95%, 100%, or any range thereof of hydroxyl protons present on hyaluronan can be deprotonated and subsequently alkylated or fluoroalkylated.

After the hyaluronan starting material or derivative thereof has been treated with a base, the deprotonated hyaluronan is reacted with an alkylating agent or fluoroalkylating agent to produce the modified hyaluronan. Examples of alkylating agents include, but are not limited to, an alkyl halide. Alkyl bromides and iodides are particularly useful. Similarly, the fluoroalkylating agent can include a fluoroalkyl halide. Alkylating agents and fluoroalkylating agents commonly used in organic synthesis can be used herein.

In certain aspects, it is desirable to sulfate the alkylated or fluoroalkylated hyaluronan described above. In one aspect, the alkylated or fluoroalkylated hyaluronan is sulfated by reacting the alkylated or fluoroalkylated SAGE with a sulfating agent to produce a sulfated product. The degree of sulfation can vary from partial sulfation to complete sulfation. In general, free hydroxyl groups present on the alkylated or fluoroalkylated hyaluronan or a derivative thereof can be sulfated. In one aspect, at least one C-2 hydroxyl proton and/or C-3 hydroxyl proton is substituted with a sulfate group. In another aspect, the degree of sulfation is from 0.5, 1.0, 1.5, 2.0, 2.5, 3.0, 3.5 or any range thereof per disaccharide unit of the alkylated or fluoroalkylated hyaluronan. In one aspect, the alkylated or fluoroalkylated SAGE can be treated with a base to deprotonate one or more hydroxyl protons followed by the addition of the sulfating agent. The sulfating agent is any compound that reacts with a hydroxyl group or deprotonated hydroxyl group to produce a sulfate group. The molecular weight of the hyaluronan can vary depending upon reaction conditions. In one aspect, the molecular weight of the SAGE is from 2 kDa to 500 kDa, 2 kDa to 250 kDa, 2 kDa to 100 kDa, 2 kDa to 50 kDa, 2 kDa to 25 kDa, or from 2 kDa to 10 kDa.

In one aspect, the alkyl group of the SAGE is methyl and at least one C-2 hydroxyl proton and/or C-3 hydroxyl proton of hyaluronan is substituted with a sulfate group. In another aspect, the alkyl group of the SAGE is methyl, at least one C-2 hydroxyl proton and/or C-3 hydroxyl proton of hyaluronan is substituted with a sulfate group, and the compound has a molecular weight of 2 kDa to 200 kDa after alkylation.

Any of the sulfated and alkylated/fluoroalkylated hyaluronan useful herein can be the pharmaceutically acceptable salt or ester thereof. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula I to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —(CO)$NH_2$, —(CO)NHR and —(CO)$NR_2$, where R is an alkyl group defined above, can be prepared by reaction of the carboxylic acid-containing compound with ammonia or a substituted amine. Also, the esters can be fatty acid esters. For example, the palmitic ester has been prepared and can be used as an alternative esterase-activated prodrug.

The sulfated polysaccharide described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. For example, the pH of the composition is from about 5 to about 6, which is suitable for topical applications. Additionally, the pharmaceutical compositions can include carriers, thickeners, diluents, preservatives, surface active agents and the like in addition to the compounds described herein.

The pharmaceutical compositions can also include one or more active ingredients used in combination with the sulfated polysaccharide described herein. The resulting pharmaceutical composition can provide a system for sustained, continuous delivery of drugs and other biologically-active agents to tissues adjacent to or distant from the application site. The biologically-active agent is capable of providing a local or systemic biological, physiological or therapeutic effect in the biological system to which it is applied. For example, the agent can act to control and/or prevent infection or inflammation, enhance cell growth and tissue regeneration, control tumor growth, act as an analgesic, promote anti-cell attachment, reduce alveolar bone and tooth loss, inhibit degeneration of cartilage and weight bearing joints, and enhance bone growth, among other functions. Additionally, any of the compounds described herein can contain combinations of two or more pharmaceutically-acceptable compounds. Examples of such compounds include, but are not limited to, antimicrobial agents, antiinflammatory agents, anesthetics, and the like. Methods for using these compositions as drug delivery devices is described in detail below.

The pharmaceutical compositions can be prepared using techniques known in the art. In one aspect, the composition is prepared by admixing a sulfated polysaccharide with a pharmaceutically-acceptable compound and/or carrier. The term "admixing" is defined as mixing the two components together so that there is no chemical reaction or physical interaction. The term "admixing" also includes the chemical reaction or physical interaction between the compound and the pharmaceutically-acceptable compound. Covalent bonding to reactive therapeutic drugs, e.g., those having nucleophilic groups, can be undertaken on the compound. Second, non-covalent entrapment of a pharmacologically active agent in a cross-linked polysaccharide is also possible. Third, electrostatic or hydrophobic interactions can facilitate retention of a pharmaceutically-acceptable compound in the compounds described herein.

The sulfated polysaccharide can be administered in a number of ways depending on whether local or systemic treatment is desired, and on the area to be treated. Administration can be topically (including ophthalmically, vaginally, rectally, intranasally, orally, or directly to the skin). Formulations for topical administration can include ointments, lotions, creams, gels, drops, suppositories, sprays, liquids and powders. Conventional pharmaceutical carriers, aqueous, powder or oily bases, thickeners and the like can be necessary or desirable. Administration can also be directly into the lung by inhalation of an aerosol or dry micronized powder.

The sulfated polysaccharide can also be injected parenterally either intravenously, subcutaneously, intramuscularly, intradermally, intranasally, or intrathecally. In other aspects, the sulfated polysaccharide is administered rectally by an enema, suppository, catheter, needleless syringe, or bulb syringe. In another aspect, the sulfated polysaccharide is formulated as a spray, wash, lavage, or other suitable formulations typically used in nasal applications.

It will be appreciated that the actual preferred amounts of the sulfated polysaccharide in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999). For example, when administered intravenously the dosage of the sulfated polysaccharide can be from 25 mg/kg to 500 mg/kg. In another aspect, when administered orally the dosage of the sulfated polysaccharide can be from 500 mg/kg to 3,000 mg/kg. In another aspect, when administered topically the dosage of the sulfated polysaccharide can be from 1% w/v to 20% w/v. In another aspect, the sulfated polysaccharide or a pharmaceutically acceptable salt or ester thereof is administered to the subject in the amount of 1 mg/kg to 500 mg/kg per single dose, 3 mg/kg to 300 mg/kg per single dose, or 10 mg/kg to 100 mg/kg per single dose.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process.

I. Administration of Modified Hyaluronan Pre- and Post-Irradiation

Materials and Methods

Modified Hyaluronan

Modified hyaluronan (referred to herein as GM-1111) used to treat the animals is a sulfated hyaluronan methylated at the primary C-6 hydroxyl position of an N-acetyl-glucosamine residue and having a molecular weight of approximately 5.5 kDa. Hyaluronic acid (HA, Novozymes, Denmark) was degraded to low molecular weight comparable to GM-1111.

Animals

Approximately 7-8 weeks of old male BDF1 (B6D2F1) mice were purchased from Charles River Laboratories (MA). These animals were housed in a room with fully controlled environment (temperature, humidity, and light/dark cycle). The feed and water were freely accessible to all animals throughout the entire study period. All animals were acclimatized for one week prior to the irradiation and they were approximately 8-10 weeks old at the time of the study. The experimental protocol (16-07008) was approved by the University of Utah Institutional Animal Care and Use Committee (IACUC).

Irradiation and Drug Dosing

Prior to the x-ray irradiation, all animals except the healthy control group were gently guided into a restrainer for short durations. This behavioral training was held once daily for two days and it was designed to reduce potential stresses on the animals during the once daily irradiation session. For head-only irradiation, the restrainers containing the animals were shielded with a lead block that had rectangular holes to expose the head. X-rays were generated by RS2000 Biological Research Irradiator (Rad Source Technologies, GA) with parameters set as 160 kV/25 mA. For study (1), the animals were divided into 4 groups (10 mice for each group)—vehicle (phosphate buffered saline) treated healthy, vehicle treated ROM, GM-1111 treated ROM, and HA treated ROM. All animals in these groups were subcutaneously administered once daily with either vehicle or drug from day −2 to 7. Both GM-1111 and HA were dissolved in PBS and dosed at 30 mg/kg (body weight). For study (2), the animals were divided into 6 groups (10 mice for each group) according to the drug dosing regimen: vehicle treated healthy (from day −2 to 7), vehicle treated ROM (from day −2 to 7), GM-1111 pre/post-irradiation (from day −2 to 7), GM-1111 pre-irradiation (from day −2 to 0), and GM-1111 post-irradiation (from day 1 to 7 or day 3 to 7). On day 0, the animals within x-ray irradiation groups (ROM) were irradiated once at a dosage of 20 Gy with 1.9 Gy/min dose rate.

Monitoring of Clinical Signs and Tissue Harvest

Body weights of the animals were measured every other day from 2 days prior to the first irradiation day (day 0). Clinical signs were monitored every day during the entire experimental period. On day 8, all animals were euthanized by exsanguination by severing the caudal vena cava under deep isoflurane anesthesia. Tongues and submandibular salivary glands were excised from each animal. To visualize the ulcerative lesion in the tissue, tongue samples were stained with 1% (w/v) Toluidine Blue, photographed on the dorsal side and then cut into half longitudinally. One side of the dissected tongue sample was then fixed in 4% neutral formalin along with salivary glands for histological examination and the other half was stored at −20° C. in a 24-well tissue culture plate for biochemical analysis.

Histology

Tissue processing for histology including paraffin embedding, cutting, and staining were carried out by Charles River Laboratories (Wilmington, Mass.). Paraffin embedded tissues were sectioned at 4 μm thickness and stained with hematoxylin and eosin (H&E).

Biochemical Analyses

All tongue samples were thawed on ice prior to homogenization. Each tongue sample was chopped into small pieces with a razor blade and suspended in ice cold PBS supplemented with glycerol (10% v/v) as well as protease inhibitor cocktail (Promega G6521, WI). Tissues were then homogenized with zirconium beads using a Bead Bug™ shaker and then centrifuged at 12,000 rpm for 5 min (4° C.). The resulting supernatant was then collected. The total protein concentration of the supernatant was measured for each sample using the Pierce™ Protein Assay kit. Tissue concentrations of IL-6 and myeloperoxidase (MPO) were then determined with commercially available ELISA kits: IL-6 (BioLegend, CA) and MPO (R&D Systems, MN).

Statistical Analyses

Body weights of the animal were converted into percent body weights compared to the values on day 0. Tissue concentrations of IL-6 and MPO were normalized by the total protein concentration of each sample. The resulting values from respective irradiation groups were treated as parametric data and compared by one-way analysis of variance test followed by Tukey's multiple comparison test. The data points that fell below the detection limit observed in IL-6 measurements were substituted with calculated numbers by an imputation method proposed by Hornung and Reed (Estimation of Average Concentration in the Presence of Nondetectable Values. *Applied Occupational Environmental Hygiene*, (1990) 5:46-51:

Substitution value=Detection Limit/√2

Histological observations were graded for each category and the sum of these grades was used to designate the severity of each sample. The resulting severity scores from all irradiation groups were analyzed with Kruskal-Wallis test followed by Dunnett-type multiple comparison test using nparcomp package. Statistical calculations were done with R statistics package (Version 3).

Results

Study (1)

Necropsy findings. The animals treated with vehicle and irradiated with x-rays developed severe ROM as evidence by the ulcerative lesions observed in necropsy (FIG. 1). The lesions were prominent in the caudal third (back of the tongue) of the tongue when visualized with Toluidine Blue staining. GM-1111 treated animals had much smaller lesions compared to the vehicle treatment group suggesting that the drug treatment reduced the development of ROM. By contrast, the animals treated with HA showed severe ulcerative lesions in the tongue similar to the vehicle treated animals suggesting the therapeutic benefits of GM-1111 in reducing oral mucositis in mice.

Figure 2:
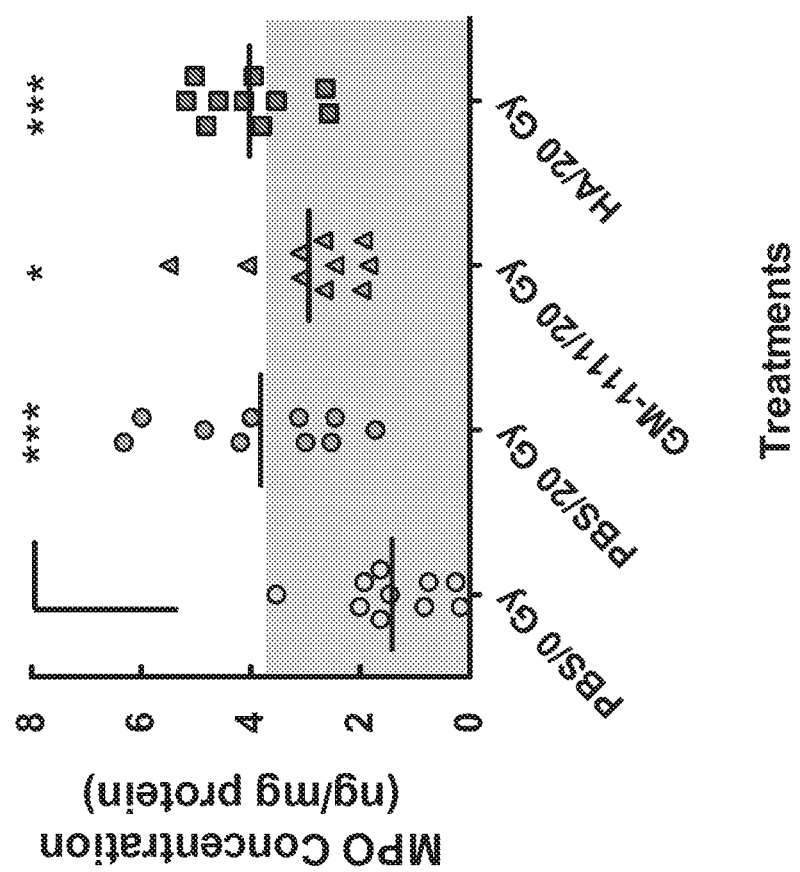
FIG. 2 shows tissue concentrations of myeloperoxidase (MPO) in the tongue. MPO in the tissue homogenate was measured by ELISA and the concentrations were normalized to the total protein concentrations of the tongues from individual animals. The tongue samples from x-ray irradiated (20 Gy) animals had significantly elevated levels of MPO compared to the healthy tissues (normal levels are shown in the gray shaded area). Few animals in GM-1111 treated group had elevated tissue MPO levels than vehicle or HA treated group. *$p<0.05$ and ***$p<0.001$ (Dunnet's t-test).

Biochemical analysis. To quantify the severity of the acute inflammation in the tongue, the tissue concentrations of myeloperoxidase (MPO) in the tongue was determined. MPO is produced and released by polymorphonuclear leukocytes (PMNs). The increased number of PMNs in the tissue is a strong evidence of active inflammation in the tissue. Tissue concentrations MPO in the x-ray irradiation group were significantly higher (50% of the animals) than the healthy animals (FIG. 2). The tongue MPO levels of GM-1111 treated animals were much less affected as only 20% of the tongue samples had higher than normal range of MPO in the tongue. By contrast, about 70% of the HA treated animals had higher than normal MPO levels in the tongue. These data suggest that GM-1111 can reduce the tissue inflammation.

Figure 3:
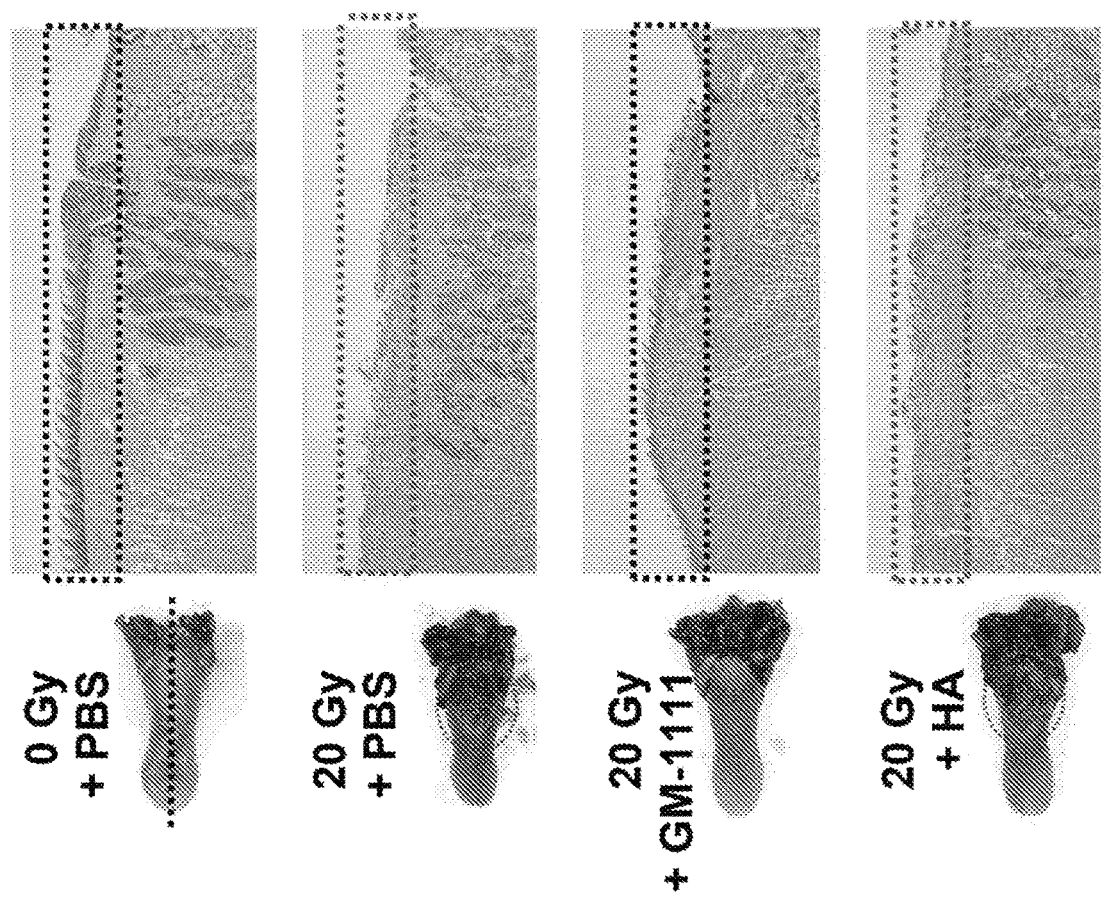
FIG. 3 shows radiation induced near complete destruction of the epithelial layer (dotted areas) in the tongue (black vs. red). These devastating changes were much mild in GM-1111 treated animals. By contrast, the epithelial layer of the tongue from HA treated animal was markedly pronounced similar to the vehicle treated group. *Hematoxylin and eosin (H&E) stained tissues (original magnification 4×). Photos show the cut surface of the tongue through the midline.

Histological examinations. To further validate the therapeutic effects of GM-1111 against ROM, the tongue tissues stained with H&E. Microscopically was examined, the radiation-induced lesions are characterized by the extensive epithelial cell death with thin mucosa, denudation of the mucosa, infiltration of PMNs into the tissue (FIG. 3, dotted area), reduced glandular contents in the salivary glands in the tongue, and occasional colonization of bacteria in the lesion. Consistent to necropsy findings and biochemical analyses of tissue MPO, the tongues from GM-1111 treated animals had much milder cell death with thicker mucosa compared to the tissues from vehicle or HA treated animals.

Conclusion

Single dose x-ray irradiation on the head induced ROM that showed marked ulcerative lesions in the tongue. The necropsy findings, biochemical analyses of MPO as well as histological examinations consistently support the anti-inflammatory effects of GM-1111 against ROM in mice. However, HA did not show any measurable therapeutic benefits against ROM.

Study (2)

Figure 4:
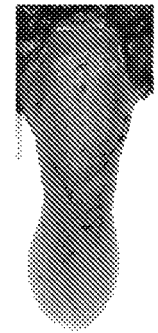
FIG. 4 shows mouse tongues (8 days after the x-ray irradiation) stained with Toluidine Blue to visualize the ulcerated lesions (marked by dotted red ovals). The tongues from vehicle (PBS) treated animals show severely ulcerated lesions. Post-irradiation treatment with GM-1111 (30 mg/kg, body weight, once daily SQ) reduced the size and the incidence rate of ROM.

Necropsy findings. Similar to study (1), the animals treated with vehicle and irradiated with x-rays developed severe ROM as evidence by the ulcerative lesions observed in necropsy (FIG. 4). A few animals treated with GM-1111 post-irradiation showed smaller ulcerative lesions than vehicle treated animals (Table 2). These therapeutic effects were observed in the animals treated with GM-1111 even 72 hrs after the irradiation or in the animals treated for 3 days (day 1 to 3). However, these effects did not appear in the animals treated with GM-1111 prior to irradiation (day −2 to 0) suggesting that GM-1111 was effective in reducing ROM when used as a post-irradiation therapeutic.

TABLE 2

| | Ulcerative lesions in the tongue* Treatment | | | | | |
|---|---|---|---|---|---|---|
| | PBS Day −2 to 7 | GM-1111 Day −2 to 0 | GM-1111 Day −2 to 7 | GM-1111 Day 1 to 7 | GM-1111 Day 3 to 7 | GM-1111 Day 1 to 3 |
| Ulcerative lesion, % (affected animals/total) | 88% (7/8) 100% (8/8) | 88% (7/8) 100% (10/10) | 20% (2/10) 10% (1/10) | 13% (1/8), 30% (3/10) | 40% (4/10) | 38% (3/8) |

*Different values in the treatment groups are from multiple experiments.

Figure 5:
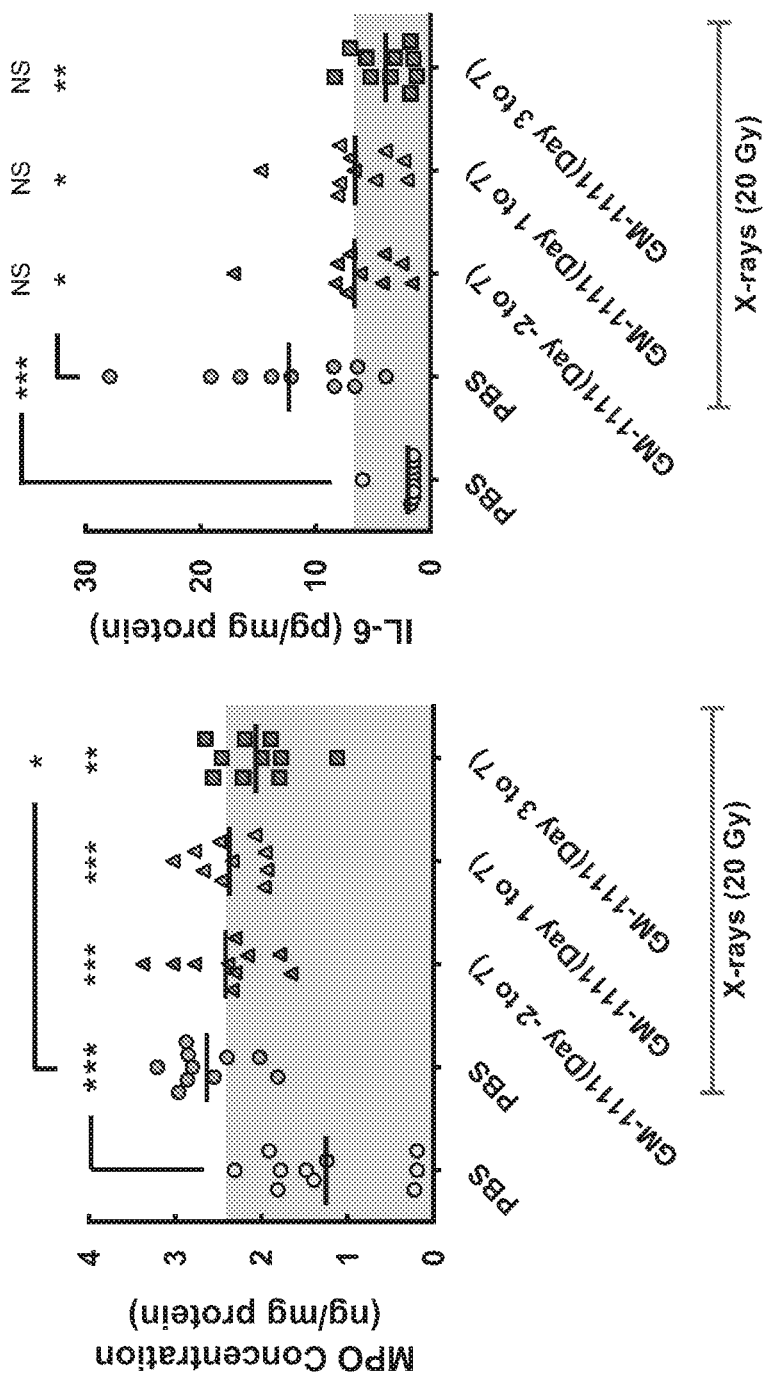
FIG. 5 shows biochemical analyses of tongue homogenates from mice treated with GM-1111 as post-irradiation dosing regimens. Both MPO and IL-6 in the tissue homogenates were measured by ELISA and the concentrations were normalized to the total protein concentrations of the tongues from individual animals. The tongue samples from x-ray irradiated (20 Gy) animals had mild but significantly elevated levels of MPO compared to the healthy tissues (normal levels are shown in the gray shaded area). Tissue IL-6 was significantly elevated only in vehicle treated group. $*p<0.05$, $p<0.01$, $*p<0.001$, and NS (not significant, p 0.05) by Tukey's test.

Biochemical analysis. To quantify the severity of the acute inflammation in the tongue, the tissue concentrations of myeloperoxidase (MPO) as well as a pro-inflammatory cytokine IL-6 in the tongue was determined. Tissue concentrations MPO in the x-ray irradiation group were significantly higher (70% of the animals) than the healthy animals (FIG. 5, left panel). Irradiation-induced rise of tissue MPO levels were much less pronounced in GM-1111 post-treated animals and a significant reduction of tissue MPO was observed in day 3-7 GM-1111 post-treatment group. Tissue levels of IL-6 was significantly increased in vehicle treated/irradiated animals (70% of the animals, FIG. 5, right panel). However, tissue levels of IL-6 in all GM-1111 post-treatment groups were comparable to the healthy animals.

Figure 6:
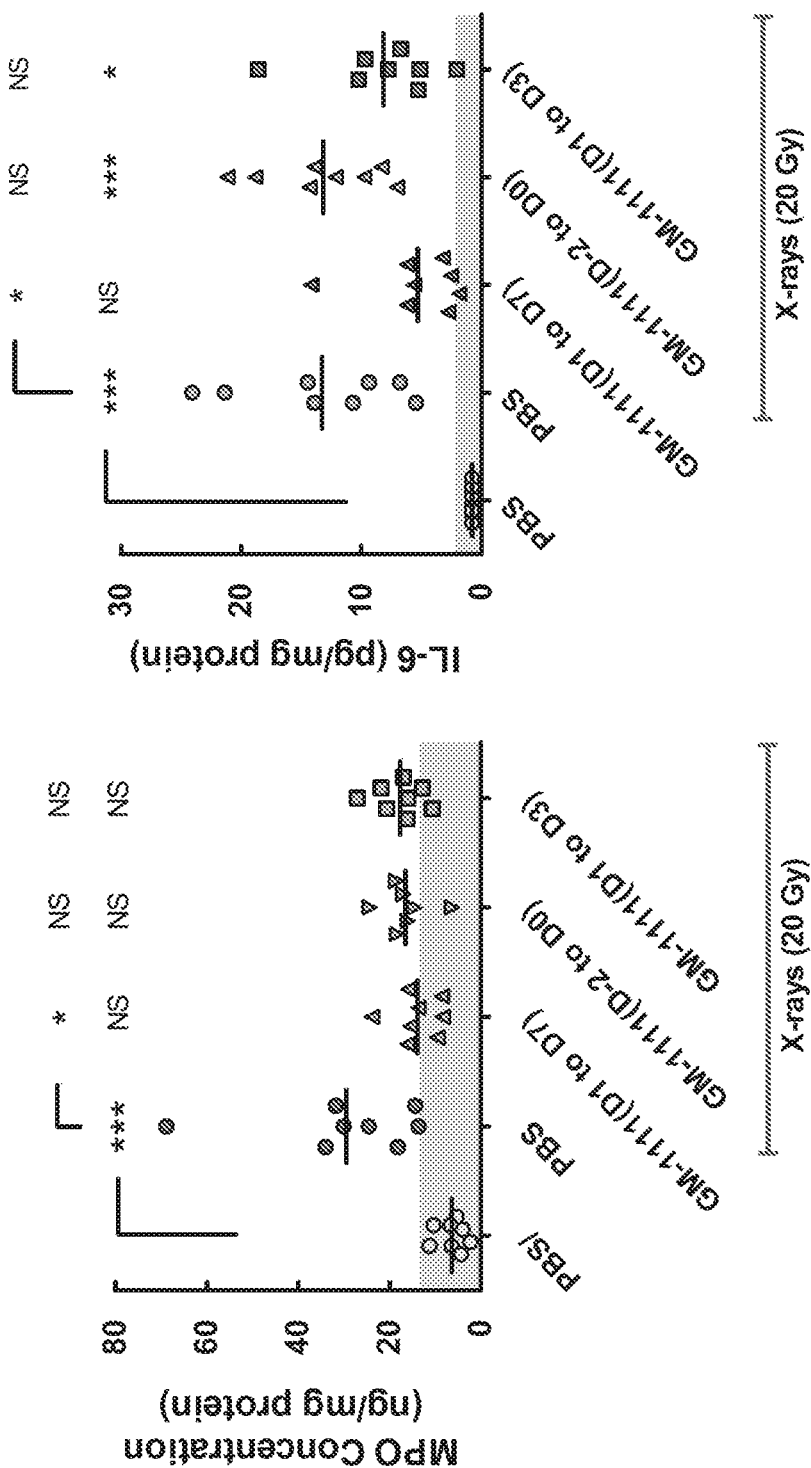
FIG. 6 shows biochemical analyses of tongue homogenates from mice treated with GM-1111 as pre-irradiation dosing regimens. Both MPO and IL-6 in the tissue homogenates were measured by ELISA and the concentrations were normalized to the total protein concentrations of the tongues from individual animals. The tongue samples from x-ray irradiated (20 Gy) animals had significantly elevated levels of MPO compared to the healthy tissues (normal levels are shown in the gray shaded area). Irradiation-induced rise of tissue MPO was observed only in vehicle treatment group. Significant increase of IL-6 was observed in vehicle and pre-irradiation GM-1111 treatment groups. $*p<0.05$, $p<0.01$, $*p<0.001$, and NS (not significant, p 0.05) by Tukey's test.

In a separate set of experiments, mice were doped with GM-1111 for 3 days prior to the irradiation to investigate the possibility of using GM-1111 as a prophylactic to ROM. Also, a group of mice was doped with GM-1111 for 3 days after the irradiation to determine whether short-term treatment after the irradiation could mitigate ROM. While the tissue MPO level in pre-irradiation GM-1111 dosing group was lower than the vehicle/irradiation group, the tissue IL-6 level was comparable to the vehicle/irradiation group (FIG. 6). By contrast, dosing for 3 days post-irradiation resulted in reduced tissue MPO as well as IL-6 levels demonstrating that post-irradiation dosing GM-1111 could mitigate the rise of pro-inflammatory biomarkers in ROM.

Figure 7:
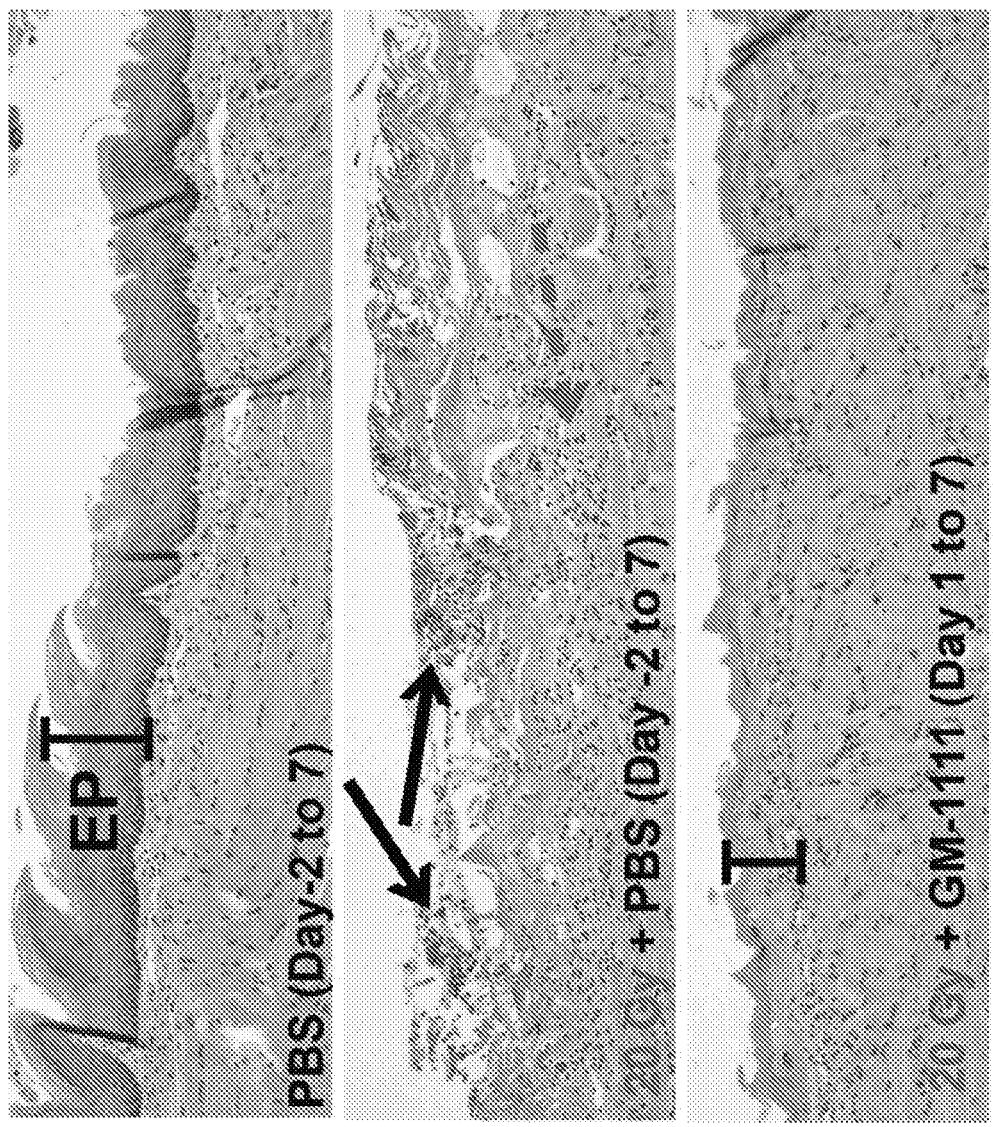
FIG. 7 shows microscopical images of acute x-ray induced ROM. Irradiation-induced injury is characterized by destruction of epithelial layer (EP) as well as infiltration of polymorphonuclear leukocytes (PMNs) in the epithelial layer and the lamina propria (red dotted arrow, middle panel). The affected lesions frequently infected and show microbial colonization (purple plaques, black arrow) forming a pseudomembrane with the fibrous tissue. Post-irradiation treatments with GM-1111 reduced radiation-induced epithelial cell death (middle vs. bottom panel). Tissues were stained with hematoxylin and eosin (H&E, original magnification 4×).

Histological examinations. Microscopical examinations of the tongues demonstrated that strong anti-inflammatory effects observed in the animals treated daily with GM-1111 from 24 hrs after the irradiation to the end of the experiment (day 1 to 7, FIG. 7). These effects were less pronounced in mice treated post-irradiation for short period of time and unobservable in mice treated with GM-1111 only prior to the irradiation. These observations suggest that GM-1111 is mostly effective in reducing ROM when used after the irradiation.

Conclusion

Mice were treated with GM-1111 by varying dosing schedule that occurred before or after the irradiation. Necropsy observations, analyses of tissue biochemical markers for inflammation, and histological examinations consistently showed that significant radiation mitigating effects found in the animals treated after the irradiation. These mitigating effects were even observed in the animals treated with GM-1111 for a brief period of time but not found in the animals treated only before the irradiation suggesting that GM-1111 can be used as a therapeutic for ROM and its beneficial effects can be achieved when the drug is used briefly. Surprisingly, these therapeutic effects did not appear in the animals treated with GM-1111 prior to irradiation, showing the importance of the continued and continuous post-radiation treatment to the efficacy of GM-1111.

II. Dosing Studies

Materials and Methods

Animals and Husbandry

Approximately 7 week old male and female BDF1 (B6D2F1) mice were purchased from Charles River Laboratories (MA). These animals were housed in a room with fully controlled environment (temperature, humidity, and light/dark cycle) at the University of Utah (UT). The feed and water were freely accessible to all animals throughout the entire study period. All animals were acclimatized for one week prior to the irradiation and they were approximately 8 weeks old at the time of the study. The experimental protocol (16-07008) was approved by the University of Utah Institutional Animal Care and Use Committee (IACUC).

Irradiation

Prior to the x-ray irradiation, all animals except the healthy control group were gently guided into a restrainer for short durations. This behavioral training was held once daily for two days and it was designed to reduce potential stresses on the animals during the once daily irradiation session. All animals receiving x-ray irradiation were immobilized within the restrainers. For head-only irradiation, the restrainers containing the animals were shielded with a lead block that had rectangular holes to expose the head. X-rays were generated by the RS2000 Biological Research Irradiator (Rad Source Technologies, GA) with parameters set at 160 kV/25 mA. The animals in irradiation groups were irradiated once daily 8 Gy/day for 5 consecutive days at a dosage rate of 1.9 Gy/min.

Monitoring of Clinical Signs and Tissue Harvest

Body weights of the animals were measured every other day from 2 days prior to the first irradiation day (day 0). Clinical signs were monitored every day during the 5-day irradiation sessions. On day 9, all animals were euthanized by exsanguination by severing the caudal vena cava under deep isoflurane anesthesia. Tongues and submandibular salivary glands were excised from each animal. To visualize the ulcerative lesion in the tissue, tongue samples were stained with 1% (w/v) Toluidine Blue (Muanza, T. M., et al. 2005. Evaluation of radiation-induced oral mucositis by optical coherence tomography. *Clinical Cancer Research*, 11:5121-7), photographed on the dorsal side and then cut into half longitudinally. One side of the dissected tongue sample was then fixed in 4% neutral formalin along with salivary glands for histological examination and the other half was stored at −20° C. in a 24-well tissue culture plate for biochemical analysis.

Histology

Tissue processing for histology including paraffin embedding, cutting, and staining were carried out by Charles River Laboratories (Wilmington, Mass.). Paraffin embedded tissues were sectioned at 4 μm thickness and stained with hematoxylin and eosin (H&E).

Biochemical Analyses

All tongue samples were thawed on ice prior to homogenization. Each tongue sample was chopped into small pieces with a razor blade and suspended in ice cold PBS supplemented with glycerol (10% v/v) as well as protease inhibitor cocktail (Promega G6521, WI). Tissues were then homogenized with zirconium beads using a Bead Bug™ shaker and then centrifuged at 12,000 rpm for 5 min (4° C.). The resulting supernatant was then collected. The total protein concentration of the supernatant was measured for each sample using the Pierce™ Protein Assay kit. Tissue concentrations of IL-6 and myeloperoxidase (MPO) were then determined with commercially available ELISA kits: IL-6 (BioLegend, CA) and MPO (R&D Systems, MN).

Statistical Analyses

Body weights of the animal were converted into percent body weights as compared to the values on day 0. Tissue concentrations of IL-6 and MPO were normalized by the total protein concentration of each sample. The resulting values from respective irradiation groups were treated as parametric data and compared by one-way analysis of variance test followed by Tukey's multiple comparison test. The data points that fell below the detection limit observed in IL-6 measurements were substituted with calculated numbers by an imputation method proposed by Hornung and Reed ("Estimation of Average Concentration in the Presence of Nondetectable Values. *Applied Occupational Environmental" Hygiene*, (1990) 5:46-51:

$$\text{Substitution value} = \text{Detection Limit}/\sqrt{2}$$

Histological observations were graded for each category and the sum of these grades was used to designate the severity of each sample. The resulting severity scores from all irradiation groups were analyzed with Kruskal-Wallis test followed by Dunnett-type multiple comparison test using the nparcomp package. (Konietschke, F. et al. 2015. nparcomp: An R Software Package for Nonparametric Multiple Comparisons and Simultaneous Confidence Intervals. Journal of Statistical Software, 64 (DOI: 10.18637/jss.v064.i09)) Statistical calculations were done with the R statistics package (Version 3.2.2 "Fire Safety", 2015 Aug. 14).

Results

Clinical Signs

Figure 8:
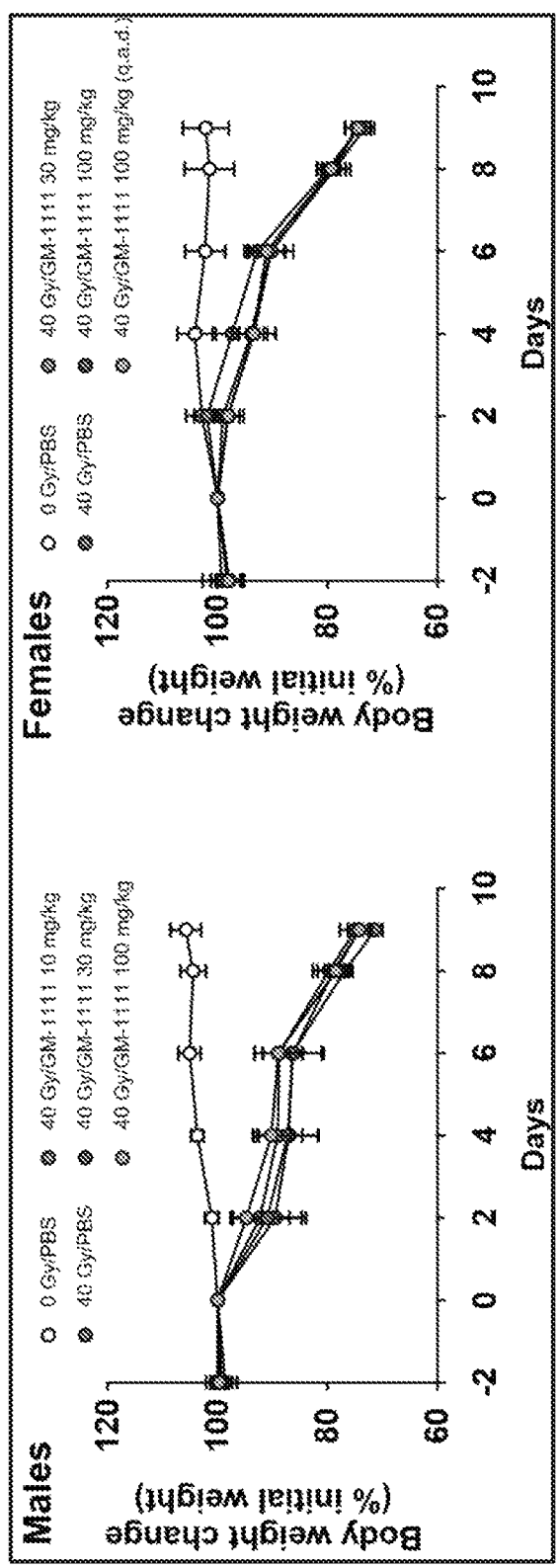
FIG. 8 shows changes of body weights in the animals receiving x-ray irradiation. Circles represent the total irradiation dosage levels. The body weight of each animal on day 0 (first x-ray irradiation) was used as 100%. Symbols and error bars represent mean values and S.D. (n=12 each).

The most apparent clinical sign attributed to the x-ray irradiation was body weight loss. Significant body weight loss was observed in all irradiation groups and appeared at two different time periods. The initial body weight loss was small and it was observed at around day 2-4 (FIG. 8). From day 6 to the end of the experiment, the animals continued to lose weight.

One female mouse in the GM-1111 (100 mg/kg, q.a.d.) dosing group was found dead on day 2 and it was regarded as an accidental death. Two female mice in the GM-1111 (100 mg/kg) dosing group were also found dead on day 8 and showed severe body weight loss and dehydration. No mortalities were observed in the male groups.

Necropsy Findings

Figures 10A, 10B, 10C:
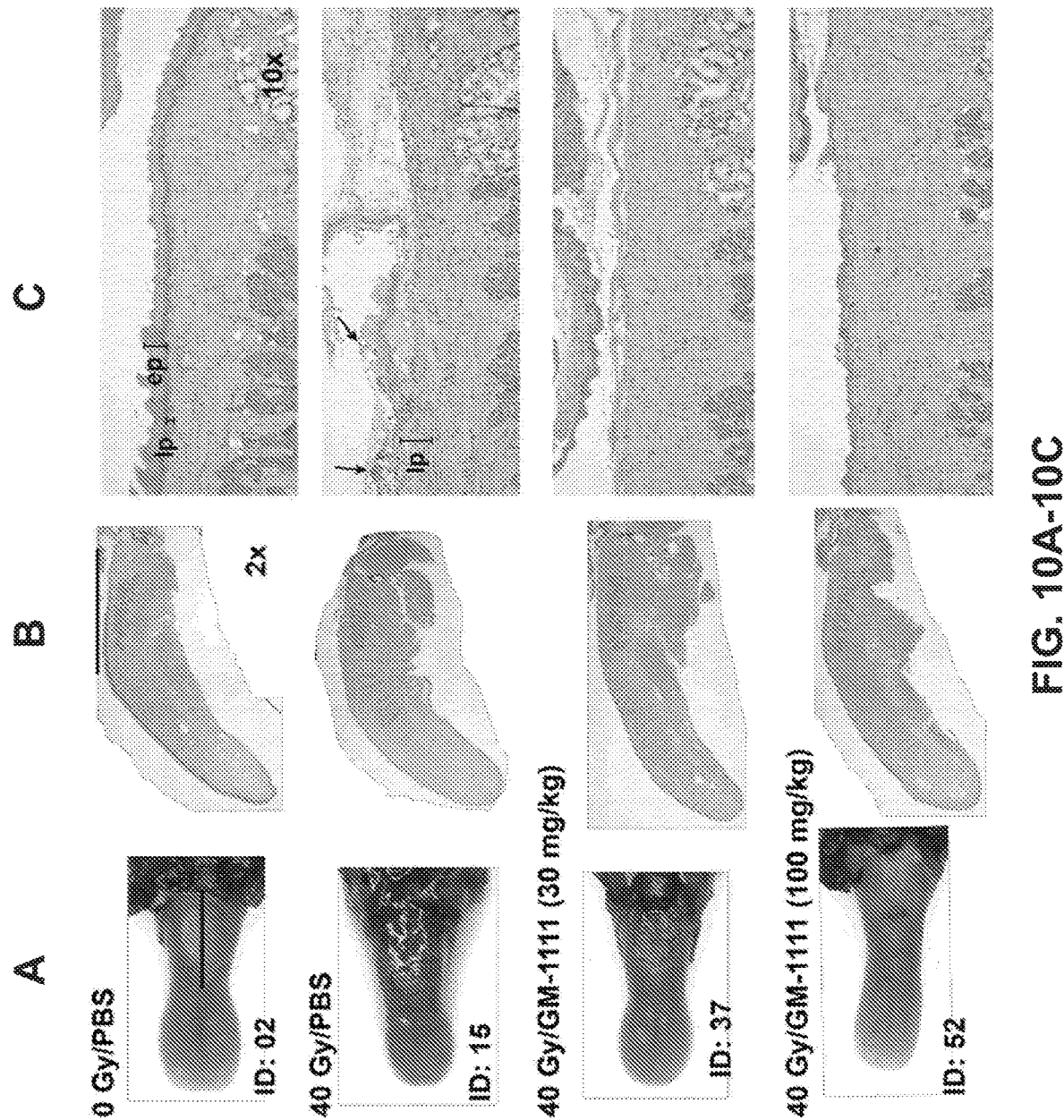
FIG. 10A-C shows photographs of gross appearance (A) and photomicrographs (B-C) of the respective tongues (males). The 40 Gy/PBS group had severely ulcerated tongues, which were characterized by a denuded epithelial layer in approximately half the length of the tongues, bacterial colonization (arrows), and a large number of infiltrated PMNs in the mucosa (second column vs. first column). The GM-1111 dosed animals showed either smaller lesions or much milder levels of inflammation in the tongue (third and fourth columns) than the PBS/irradiation group. H&E stained samples show the partial loss of epithelium (ep) in the GM-1111 dosing group and few observable PMNs in the lesion. The inflamed tissue of the 40 Gy/PBS group also showed expanded lamina propria (Ip) compared to the healthy and GM-1111 dosed groups. B, panoramic image of the longitudinal section of the tongue (original magnification, 2×) and C, higher magnification (10×) view of the rear half of the tongue (bar).

Gross examinations of both sexes of animals in all irradiated groups showed significant weight loss and dehydration. Visibly most of the animals in these groups exhibited a rough coat suggesting the lack of grooming. Fewer animals in the GM-1111 dosed animals (30 mg/kg and higher) showed a rough coat compared to the animals in the other groups. The gastrointestinal tracts in most of the irradiated animals were generally empty with a small amount of digested food. Omental fats were mostly absent suggesting malnutrition with dehydration. Salivary glands appeared smaller than normal consistent with the signs of dehydration. The tongues in the 40 Gy/PBS and 40 Gy/GM-1111 (10 mg/kg) groups were severely inflamed with varying degrees of ulcerations as visualized with Toluidine Blue staining (Table 3 and FIG. 10A/11A). These lesions were markedly smaller and less pronounced in the animals dosed with daily GM-1111 at 30 mg/kg and 100 mg/kg (Table 2). The animals receiving every other day dosing (q.a.d.) of 100 mg/kg of GM-1111 showed apparent ulcerations in the tongue similar to the 40 Gy/PBS group.

TABLE 3

Gross assessment of lingual inflammation.

| Groups | Mucosal Erosion (affected animals/total)* | |
| --- | --- | --- |
| (Irradiation/Drug treatment) | Males | Females |
| 0 Gy/PBS | 0/12 (0%) | 0/12 (0%) |
| 40 Gy/PBS | 12/12 (100%) | 11/12 (92%) |
| 40 Gy/GM-1111 10 mg/kg | 11/12 (92%) | N/A |
| 40 Gy/GM-1111 30 mg/kg | 6/12 (50%) | 3/12 (25%) |
| 40 Gy/GM-1111 100 mg/kg | 1/12 (8%) | 2/10 (20%) |
| 40 Gy/GM-1111 100 mg/kg (q.a.d.) | N/A | 10/11 (91%) |

*Tongues were stained with Toluidine Blue to visualize the erosion of the mucosal layer. Moderate to large ulcerative lesions were counted as positive for mucosal erosion.

Biochemical Markers in the Tissues

As quantitative measures of tissue inflammation, we determined the tissue concentrations of a pro-inflammatory cytokine IL-6 as well as myeloperoxidase (MPO) from polymorphonuclear leukocytes (PMNs or neutrophils) in the tongue homogenates.

Figure 9:
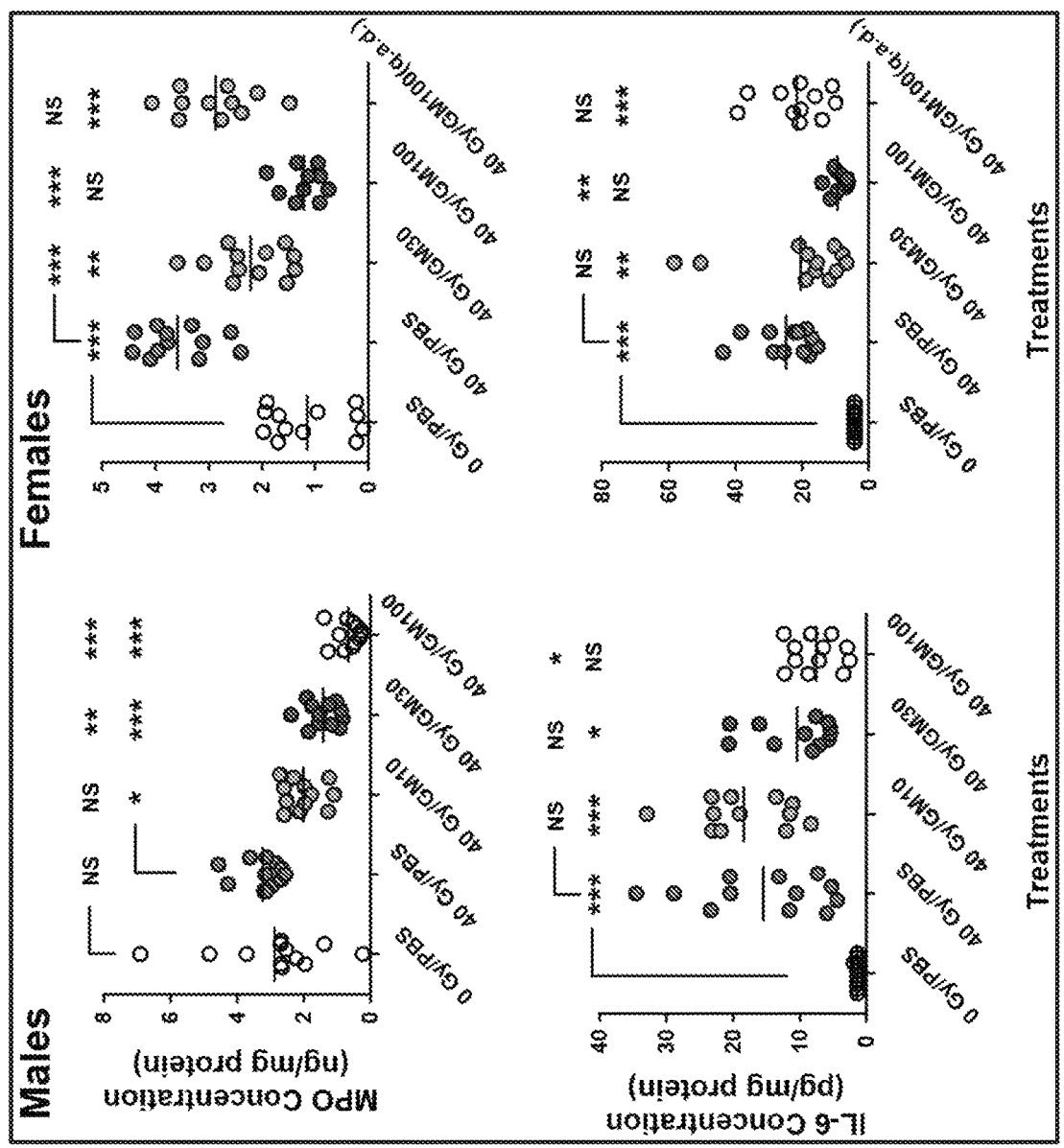
FIG. 9 shows changes of tissue biochemical markers of inflammation in the tongue homogenates. Both tissue MPO and IL-6 levels in the tongue (top panels) are elevated in the 40 Gy/PBS group compared to the healthy control (0 Gy/PBS) group. GM-1111 dosed groups show decreased concentrations of MPO and IL-6 in the tissue. Symbols represent the measured values from each animal. Horizontal bars are mean values of each group. NS, not significant (p>0.05), $*p<0.05$, $p<0.01$, and $*p<0.001$ compared to the respective controls (0 Gy/PBS or 40 Gy/PBS).

The tissue concentrations of MPO in the tongue homogenates showed a radiation-induced increase and a GM-1111 dose-dependent reduction was observed in the 30 mg/kg and 100 mg/kg dosed groups (both sexes, FIG. 9 top panel). The tissue MPO concentrations in the male GM-1111 dosed groups were lower than the healthy control group. The irradiation-induced reduction of MPO is likely caused by the disappearance of the granulocytes in the hyoid bone that are extremely sensitive to ionizing radiations. While the irradiation-damaged mucosal tissue of the tongue is infiltrated with PMNs, the affected bone marrow in the hyoid bone loses granulocytes that are also an additional source of MPO in the tongue homogenate. To reduce this issue, the rear portion of the tongue that harbored the hyoid bone in female tissue samples was removed. The MPO concentrations in the GM-1111 dosed groups were comparable to the healthy control group.

Similar to tissue MPO concentrations, the concentrations of IL-6 in the tongue homogenate were generally increased in all irradiated animals with the highest increase observed in the PBS/irradiation group. GM-1111 treatments reduced irradiation-induced IL-6 release and the reduction was GM-1111 dosage dependent. Marked reductions of radiation-induced IL-6 release were observed in the 30 mg/kg and 100 mg/kg (both sexes) GM-1111 dosed groups.

Histological Examinations

Figures 11A, 11B, 11C:
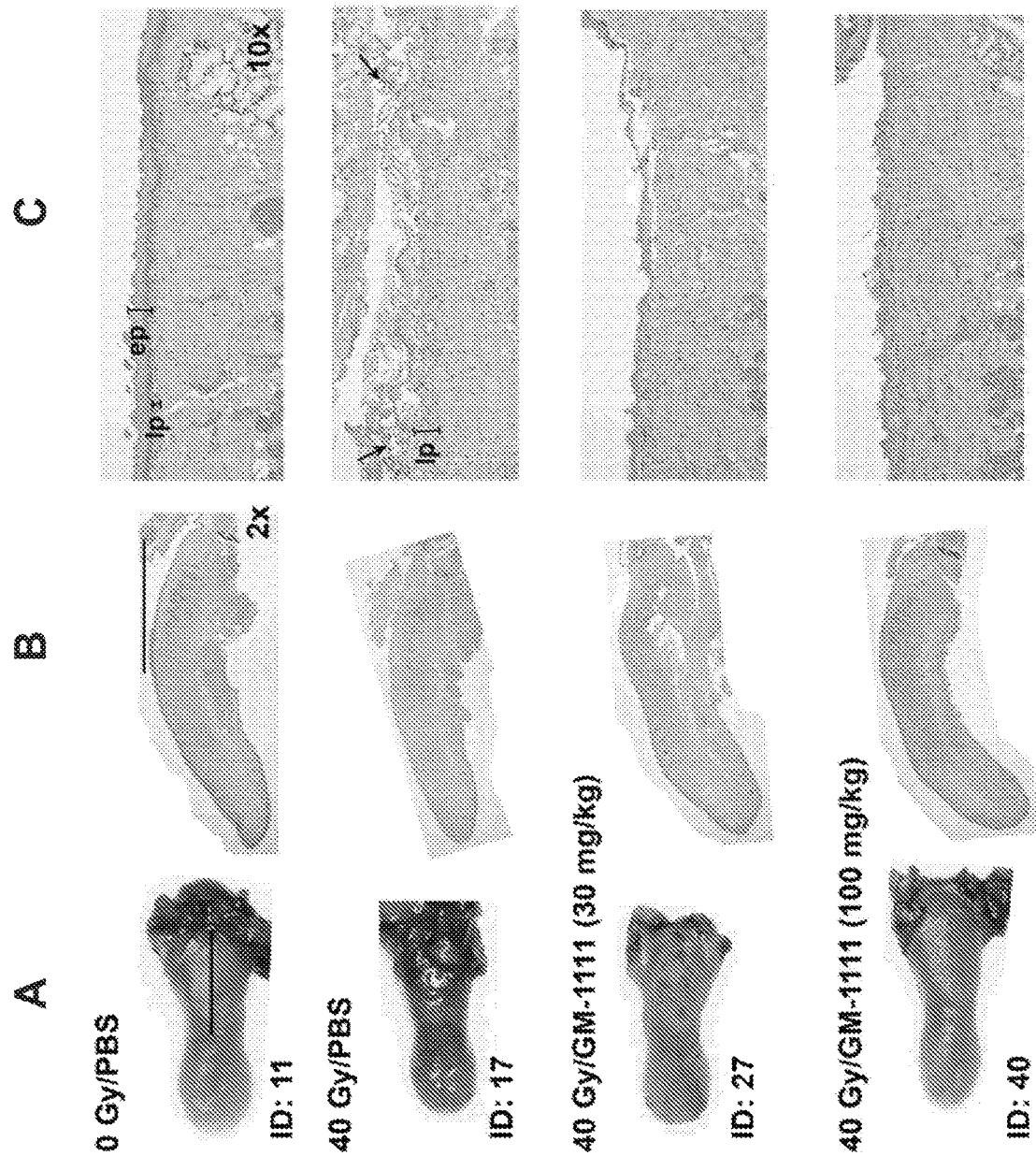
FIG. 11A-C shows photographs of gross appearance (A) and photomicrographs (B-C) of the respective tongues (females). The 40 Gy/PBS group had severely ulcerated tongues, which were characterized by denuded epithelial layer in approximately half the length of the tongues, bacterial colonization (arrows), and a large number of infiltrated PMNs in the mucosa (second column vs. first column). The GM-1111 dosed animals showed either smaller lesions or much milder levels of inflammation in the tongue (third and fourth columns) than the PBS/irradiation group. H&E stained samples show the partial loss of epithelium (ep) in the GM-1111 dosing groups and few observable PMNs in the lesion. The inflamed tissue of the 40 Gy/PBS group also showed expanded lamina propria (Ip) compared to the healthy and GM-1111 dosed groups. B, panoramic image of the longitudinal section of the tongue (original magnification, 2×) and C, higher magnification (10×) view of the rear half of the tongue (bar).
Figure 12:
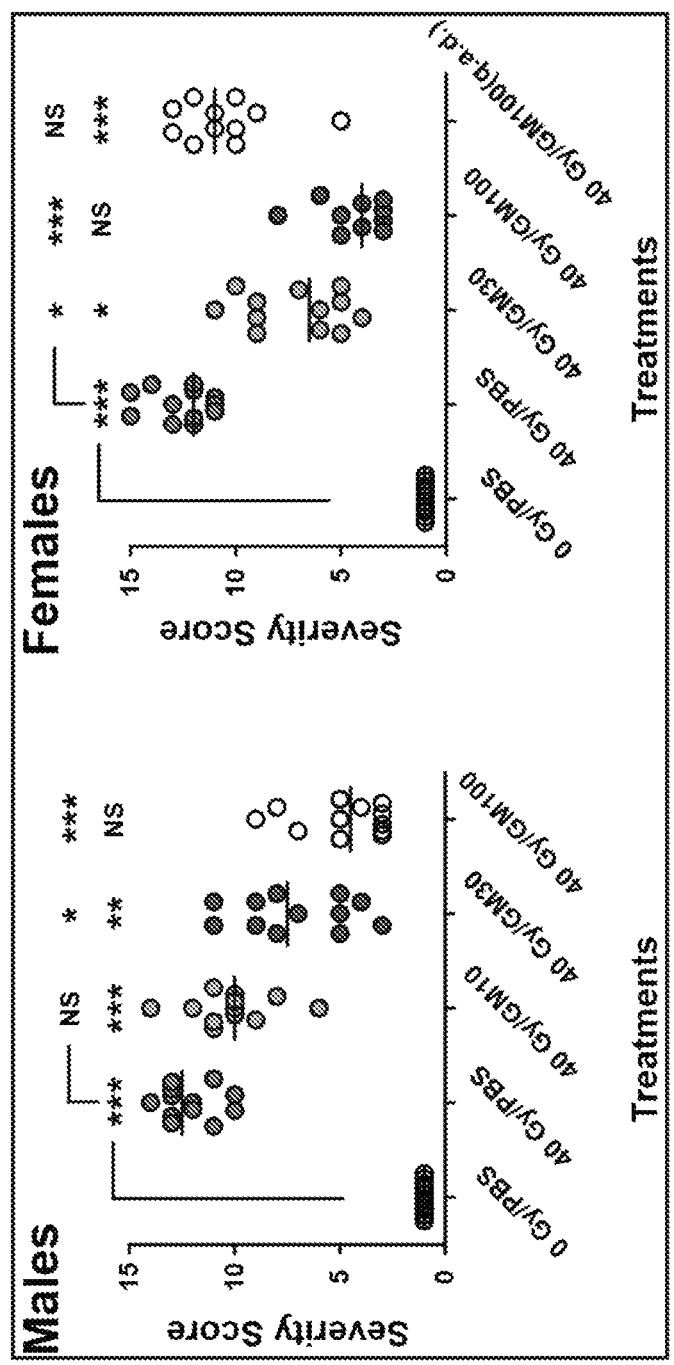
FIG. 12 shows the statistical analyses of histology severity scores. Horizontal lines are the median values in each group. NS, not significant, $*p<0.05$, $p<0.01$, and $*p<0.001$ compared to the respective controls (0 Gy/PBS or 40 Gy/PBS).

Tongue samples from the irradiation groups had various inflammatory changes. The most notable changes were the erosion of the epithelium due to the cell death that often resulted in the denudation of the epithelium in the affected area (FIGS. 10 and 11). The lesions were often accompanied with bacterial colonization and marked infiltration of leukocytes that were primarily PMNs. In a few cases, mucous glands in the tongue showed less glandular content in the cytoplasm. Serous glands showed multiple frequent cell deaths and mitotic cells in the PBS/irradiation group. By contrast, the tissues from GM-1111 dosed (30 and 100 mg/kg) animals showed mild inflammatory changes with an intact keratinized layer on the surface and often had epithelial cells in the mucosa. The infiltrated PMNs in these tissues were also limited and the thickness of the lamina propria was largely unaffected. Tissue damage caused by irradiation and the reduced damage observed in GM-1111 dosing groups were similar in both sexes of animals. The severity of lesions was scored for each tissue sample according to the degree of mucosal erosion, the number of PMNs in the lesion, and the alterations in the salivary glands in the tongue. The statistical analyses of the severity score showed a significant increase of the score for the 40 Gy/PBS group (FIG. 12). By contrast, the severity scores for the GM-1111 dosed groups were significantly decreased suggesting reduced inflammation in the tissue.

Conclusions

ROM was successfully induced with fractionated x-ray irradiation in both sexes of mice: large ulcerative lesions in the necropsy findings, increased concentrations of MPO as well as IL-6 in the tongue homogenates, and severe inflammatory lesions observed in the histological examinations were consistent to the previous studies. In the current model of fROM, the anti-inflammatory effects of GM-1111 were shown in all measured parameters. The daily administration of GM-1111 at 30 m/kg was sufficient to reduce fROM in both sexes of mice.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for preventing a serious health consequence, tissue damage, or a combination thereof in a subject exposed to ionizing radiation, chemotherapy, or a combination thereof comprising administering to the subject a sulfated polysaccharide or a pharmaceutically acceptable salt or ester thereof after the subject has been exposed to ionizing radiation, chemotherapy, or a combination thereof, wherein the sulfated polysaccharide or a pharmaceutically acceptable salt or ester thereof comprises a modified hyaluronan or a pharmaceutically acceptable salt or ester thereof, wherein the modified hyaluronan or its pharmaceutically acceptable salt or ester comprises (a) a sulfated hyaluronan or the pharmaceutically acceptable salt or ester thereof or (b) hyaluronan comprising at least one sulfate group and at least one primary C-6 hydroxyl position of an N-acetyl-glucosamine residue comprising an alkyl group or fluoroalkyl group, and wherein the subject is not administered hyaluronic acid, and wherein the sulfated polysaccharide or the pharmaceutically acceptable salt or ester thereof is administered vaginally, rectally, intranasally, or orally to the subject.

2. The method of claim 1 wherein the serious health consequence comprises acute radiation syndrome (ARS).

3. The method of claim 1, wherein the source of the ionizing radiation is produced during the production of nuclear energy, an atomic detonation test, a terrorist act, an act of war, during the transport and storage of a radioactive material.

4. The method of claim 1, wherein the ionizing energy is used in a diagnostic application or therapeutic application or the source of the ionizing radiation is radiation provided to a cancer patient.

5. The method of claim 1, wherein the source of the ionizing radiation comprises cosmic radiation.

6. The method of claim 1, wherein the source of the ionizing radiation is produced during the extraction or processing of an ore, the mining of phosphate, the mining of coal or the burning of coal, the extraction of rare earth metals, the extraction of oil or natural gas, the mining of zircon and zirconia, or the mining of radium and thorium.

7. The method of claim 1, wherein the tissue comprises a mucosal membrane in the subject or the skin of the subject.

8. The method of claim 1, wherein the tissue is in the mouth, salivary glands, mucosal glandular tissues, sinus, lungs, intestine, vagina, anus, rectum, or urinary tract of the subject.

9. The method of claim 1, wherein the sulfated polysaccharide is formulated into an ointment, cream, gel, mouthwash, capsule, film, patch, suppository, enema, aerosol or spray.

10. The method of claim 1, wherein the sulfated polysaccharide or a pharmaceutically acceptable salt or ester thereof is initially administered to the subject within 0.5 hours to 48 hours after exposure to radiation, chemotherapy, or a combination thereof.

11. The method of claim 1, wherein the sulfated polysaccharide or a pharmaceutically acceptable salt or ester thereof is administered to the subject daily for up to 10 days after exposure to radiation, chemotherapy, or a combination thereof.

12. The method of claim 1, wherein the sulfated polysaccharide or a pharmaceutically acceptable salt or ester thereof prevents oral mucositis.

13. The method of claim 1, wherein (1) 100% of the primary C-6 hydroxyl protons of the N-acetyl-glucosamine residue of the sulfated hyaluronan are substituted with a sulfate group, (2) the sulfated hyaluronan has a degree of sulfation from 3.0 to 4.0, and (3) the sulfated hyaluronan has an average molecular weight from 1 kDa to 3 kDa.

14. The method of claim 1, wherein the sulfated polysaccharide or a pharmaceutically acceptable salt or ester thereof is administered to the subject prior to exposure to the ionizing radiation.

15. The method of claim 1, wherein the sulfated polysaccharide or a pharmaceutically acceptable salt or ester thereof is administered to the subject from 0.5 hours to 72 hours subsequent to the initial exposure to ionizing radiation.

16. A method for preventing a serious health consequence, tissue damage, or a combination thereof in a subject exposed to ionizing radiation, chemotherapy, or a combination thereof comprising administering to the subject a sulfated polysaccharide or a pharmaceutically acceptable salt or ester thereof after the subject has been exposed to ionizing radiation, chemotherapy, or a combination thereof,
wherein the sulfated polysaccharide or a pharmaceutically acceptable salt or ester thereof comprises a modified hyaluronan or a pharmaceutically acceptable salt or ester thereof, wherein the modified hyaluronan or its pharmaceutically acceptable salt or ester comprises (a) a sulfated hyaluronan or the pharmaceutically acceptable salt or ester thereof or (b) hyaluronan comprising at least one sulfate group and at least one primary C-6 hydroxyl position of an N-acetyl-glucosamine residue comprising an alkyl group or fluoroalkyl group, and
wherein the subject is not administered hyaluronic acid, and
wherein the sulfated polysaccharide is formulated into an ointment, cream, gel, mouthwash, capsule, film, patch, suppository, enema, aerosol or spray.

17. The method of claim 16, wherein the source of the ionizing radiation is produced during the production of nuclear energy, an atomic detonation test, a terrorist act, an act of war, during the transport and storage of a radioactive material.

18. The method of claim 16, wherein the ionizing energy is used in a diagnostic application or therapeutic application or the source of the ionizing radiation is radiation provided to a cancer patient.

19. The method of claim 16, wherein the source of the ionizing radiation comprises cosmic radiation.

20. The method of claim 16, wherein the source of the ionizing radiation is produced during the extraction or processing of an ore, the mining of phosphate, the mining of coal or the burning of coal, the extraction of rare earth metals, the extraction of oil or natural gas, the mining of zircon and zirconia, or the mining of radium and thorium.

21. The method of claim 16, wherein the tissue comprises a mucosal membrane in the subject or the skin of the subject.

22. The method of claim 16, wherein the tissue is in the mouth, salivary glands, mucosal glandular tissues, sinus, lungs, intestine, vagina, anus, rectum, or urinary tract of the subject.

23. The method of claim 16, wherein the sulfated polysaccharide or a pharmaceutically acceptable salt or ester thereof prevents oral mucositis.

24. The method of claim 16, wherein (1) 100% of the primary C-6 hydroxyl protons of the N-acetyl-glucosamine residue of the sulfated hyaluronan are substituted with a sulfate group, (2) the sulfated hyaluronan has a degree of sulfation from 3.0 to 4.0, and (3) the sulfated hyaluronan has an average molecular weight from 1 kDa to 3 kDa.

25. The method of claim 16, wherein the sulfated polysaccharide or a pharmaceutically acceptable salt or ester thereof is administered to the subject prior to exposure to the ionizing radiation.

26. The method of claim 16, wherein the sulfated polysaccharide or a pharmaceutically acceptable salt or ester thereof is administered to the subject from 0.5 hours to 72 hours subsequent to the initial exposure to ionizing radiation.

* * * * *